United States Patent [19]

Beutler

[11] Patent Number: 5,266,459
[45] Date of Patent: Nov. 30, 1993

[54] GAUCHER'S DISEASE: DETECTION OF A NEW MUTATION IN INTRON 2 OF THE GLUCOCEREBROSIDASE GENE

[75] Inventor: Ernest Beutler, La Jolla, Calif.

[73] Assignee: The Scripps Research Institute, La Jolla, Calif.

[21] Appl. No.: 841,652

[22] Filed: Feb. 24, 1992

[51] Int. Cl.$^5$ .......................... C12Q 1/68; C07H 15/12
[52] U.S. Cl. ...................................... 435/6; 435/91.2; 935/77; 935/78; 536/23.1
[58] Field of Search ...................... 436/501.94; 536/27, 536/23.1; 435/6, 91; 935/77, 78

[56] References Cited

PUBLICATIONS

Dahl et al., "Gaucher Disease Type III (Norrbottnian Type) is Caused by a Single Mutation in Exon 10 of the Glucocerebrosidase Gene", *Am. J. Hum. Genet.*, 47:275-278 (1990).

Beutler et al., "The Facile Detection of the nt 1226 Mutation of Glucocerebrosidase by 'Mismatched' PCR", *Clin. Chim. Acta.*, 194:161-166 (1990).

Beutler, "Goucher's Disease", *New Engl. J. Med.*, 325:1354-1359 (1991).

Beutler et al., "Identification of the Second Common Jewish Gaucher Disease Mutation Makes Possible Population-based Screening for the Heterozygous State", *Proc. Natl. Acad. Sci., USA*, 88:10544-10547 (1991).

Hong et al., "Sequence of Two Alleles Responsible for Gaucher Disease", *DNA and Cell Biol.*, 9:233-241 (1990).

Horowitz et al., "The Human Glucocerebrosidase Gene and Pseudogene: Structure and Evolution", *Genomics*, 4:87-96 (1989).

Kumar et al., "Designed Diagnostic Restriction Fragment Length Polymorphisms for the Detection of Point Mutations in ras Oncogenes", *Oncogene Res.*, 1:235-241 (1989).

Latham et al., "Heterogeneity of Mutations in the Acid β-Glucosidase Gene of Gaucher Disease Patients", *DNA and Cell Biol.*, 10:15-21 (1991).

Sorge et al., "Molecular Cloning and Nucleotide Sequence of Human Glucocerebrosidase cDNA", *Proc. Natl. Acad. Sci., USA*, 82:7289-7293 (1985).

Sorge et al., "The Human Glucocerebrosidase Gene Has Two Functional ATG Initiator Codons", *Am. J. Hum. Genet.*, 41:1016-1024 (1987).

Sorge et al., "High Level Transcription of the Glucocerebrosidase Pseudogene in Normal Subjects and Patients with Gaucher Disease", *J. Clin. Invest.*, 86:1137-1141 (1990).

Theophilus et al., "Gaucher Disease: Molecular Heterogeneity and Phenotype-Genotype Correlations", *Am. J. Hum. Genet.*, 45:212-225 (1989).

Tsuji et al., "A Mutation in the Human Glucocerebrosidase Gene in Neuronopathic Gaucher's Disease", *New Engl. J. Med.*, 316:570-575 (1987).

Tsuji et al., "Genetic Heterogeneity in Type 1 Gaucher Disease: Multiple Genotypes in Ashkenazic and Non-Ashkenazic Individuals", *Proc. Natl. Acad. Sci., USA*, 85:2349-2352 (1988).

Zimran et al., "Prediction of Severity of Gaucher's Disease by Identification of Mutations at DNA Level", *The Lancet*, 2:349-352 (1989).

Zimran et al., "A Glucocerebrosidase Fusion Gene in Gaucher Disease", *J. Clin. Invest.*, 85:219-222 (1990).

*Primary Examiner*—Stephanie W. Zitomer
*Attorney, Agent, or Firm*—Douglas A. Bingham; Thomas Fitting; April C. Logan

[57] ABSTRACT

A method for detecting a new Gaucher disease mutation in an allele in a human having a point mutation of an adenine nucleotide substituted for a guanine nucleotide at nucleotide position 1 in the normal glucocerebrosidase gene intron 2 is provided. Identification of the mutation is accomplished by first amplifying, with a polymerase chain reaction (PCR) primer, a region of human genomic DNA containing nucleotide position 1 of glucocerebrosidase gene intron 2 followed by detection of the mutation.

18 Claims, No Drawings

GAUCHER'S DISEASE: DETECTION OF A NEW MUTATION IN INTRON 2 OF THE GLUCOCEREBROSIDASE GENE

This invention was made with the support of the United States Government, and the United States Government has certain rights in the invention pursuant to the National Institutes of Health Contracts DK36639 and RR00833.

DESCRIPTION

1. Technical Field

The present invention relates to a method for detecting a Gaucher disease allele in a human having an point or substitution mutation of an adenine nucleotide for a guanine nucleotide at nucleotide position 1 in the normal glucocerebrosidase gene intron 2 or also referred to as intervening sequence 2 (IVS2+1).

2. Background of the Invention

Gaucher disease is an autosomal recessive disorder caused by a deficiency of glucocerebrosidase, the enzyme that is required for the lysosomal degradation of lipids containing covalently bound sugars (glycolipids). Brady et al., *J. Biol. Chem.*, 240:39–43 (1965). In the absence of glucocerebrosidase, the extremely insoluble glucosyl-ceramide (glucocerebroside) accumulates.

The gene for glucocerebrosidase is located on chromosome-1 in the region of q21 See, Shafit-Zagardo et al., *Am. J. Hum Genet.*, 33:564–575 (1981); Ginns et al., *Proc. Natl. Acad. Sci., USA*, 82:7101–7105 (1985). The fact that a number of different mutations caused Gaucher disease was inferred from clinical observations (Beutler, *Genetic Diseases Amono Ashkenazi Jews*, eds. Boudman et al., Raven Press, NY, pp. 157–169 (1979)) and also from differences in the kinetic properties of the residual enzyme in different patients with the disorder. Grabowski et al., *Am J. Hum. Genet.*, 37:499–510 (1985). However, real understanding of the genetics of this disease has had to await the cloning and sequencing of the cDNA (Sorge et al., *Proc. Natl. Acad. Sci., USA*, 82:7289–7293 (1985) and Tsuji et al., *N. Engl. J. Med.*, 316:570–621 (1987)) and of the gene (Horowitz et al., *Genomics*, 4:87–96 (1989)). Analysis of mutations is complicated by the existence of a pseudogene which is approximately 16 kilobases (Kb) downstream from the glucocerebrosidase gene. Zimran et al., *J. Clin. Invest.*, 86:1137–1141 (1990). The pseudogene is about 95% homologous to the functional gene. It is transcribed (Sorge et al., *J. Clin. Invest.*, 86:1137–1141 (1990)), but cannot be translated into glucocerebrosidase because of numerous deletions of coding sequences.

Point mutations that cause Gaucher disease have been summarized recently. Latham et al., *DNA Cell Biol.*, 10:15–21 (1991) and Grabowski et al., *CRC Crit. Rev. Biochem. Mol Biol.*, 25:385–414 (1990. In addition, fusion genes in which the 5' sequence is that of the active gene and the 3' sequence that of the pseudogene have been documented. See, Zimran et al., *J. Clin. Invest.*, 85:219–222 (1990); Latham et al., *DNA Cell Biol.*, 10:15–21 (1991); Eyal et al., *Gene*, 96:277–283 (1990). When investigated at the genomic level, at least some such fusion genes appear to be the result of unequal crossing-over with loss of the portion of the gene between the gene and pseudogene. Zimran et al., *J. Clin. Invest.*, 85:219–222 (1990).

The disease is most prevalent in the Jewish population with a heterozygote frequency that has been estimated to approach 9%. Zimran et al., *Am. J. Hum. Genet.*, (1991). In Jewish patients with clinically significant Gaucher disease, about 77% of the disease-causing alleles contain a characteristic adenine to guanine (A→G) mutation at cDNA nucleotide position (nt) 1226 (designated the 1226G mutation) Which is in the codon coding for amino acid residue 370 of the mature protein. See, Tsuji et al., *Proc. Natl. Acad. Sci., USA*, 85:2349–2352, 5708 (1988); Zimran et al., *Lancet*, 2:349–352 (1989). The corresponding position of the mutation in the glucocerebrosidase gene is in exon 9 at nucleotide position 2. This nucleotide position in exon 9 correlates with nucleotide position 5854 in the normal glucocerebrosidase gene sequence in SEQ ID NO 1. The same mutation is also common in the non-Jewish population, where it is found to account for approximately 25% of the disease-producing alleles. This mutation is always found in a gene that also contains a characteristic RFLP (restriction fragment length polymorphisms) with the enzyme Pvu II at genomic nt 3938, suggesting that the mutation may have occurred only once. Zimran et al., *Am J. Hum. Genet.*, 46:902–905 (1990).

A second, much less common mutation is at cDNA nucleotide position 1448 where cytosine has been substituted for thymine (T→C). See, Tsuji et al., *N. Engl. J. Med.*, 316:570–621 (1987); Dahl et al., *Am. J. Hum. Genet.* 47:275–278 (1990). The corresponding position of the mutation in the functional glucocerebrosidase gene is in exon 10 at nucleotide position 60. This nucleotide position in exon 10 correlates with nucleotide position 6445 in the normal glucocerebrosidase gene sequence in SEQ ID NO 1. The 1448C mutation accounts for only about 2% of Jewish Gaucher disease producing alleles and for about 40% of the alleles in non-Jewish patients. Thus, in both Jewish and non-Jewish patients many of the Gaucher disease alleles have remained unidentified and have been designated "? ".

The T→C point mutation in the functional glucocerebrosidase gene exactly matches the sequence found normally in the glucocerebrosidase pseudogene cDNA. See Horowitz et al., *Genomics*, 4:87–96 (1989), Tsuji et al., supra, and Sorge et al., *Proc. Natl. Acad Sci., USA*, 82:7289–7293 (1985). In addition, the presence of the T→C point mutation in exon 10 has been identified in a fusion gene which was the result of rearrangement of DNA in the glucocerebrosidase gene complex. See, Zimran et al., *J. Clin. Invest.*, 85:219–222 (1990). The fusion gene resulted from an unequal cross-over event between the functional glucocerebrosidase gene and the pseudogene.

In this particular fusion gene, the 5' end of the transcribed cDNA was the functional gene and the 3' end was the pseudogene. The cross-over event occurred 5' or upstream to exon 10. Thus, the region of the pseudogene containing the cytosine nucleotide corresponding to the point mutation in the functional gene is in the 3' region of the fusion gene. In this situation, the nucleotide position of the cytosine nucleotide would not alter. However, if an unequal cross-over event occurs sufficiently 5' to the mutation, the nucleotide position of the mutation in exon 10 may change. Therefore, the designation of nucleotide position 60 in exon 10 corresponding to nucleotide position 1448 in the cDNA would no longer be accurate. However, the region surrounding the mutation would be found in the same context, i.e., the surrounding nucleotides would be the same.

Another mutation more common than the cDNA 1448C mutation was recently identified. See Beutler et al., *N. Engl. J. Med.*, 325:1354-1359 (1991) and Beutler et al., *Proc. Natl. Acad. Sci., USA*, 88:10544-10547 (1991). The mutation is a guanine nucleotide insertion adjacent to the guanine normally present at nucleotide position 57 in exon 2 of the glucocerebrosidase gene. Another way of expressing this is that nucleotide position 57 (nt57) of exon 2 is occupied by one or two nucleotides. In the normal (wild type) gene, nt 57 is occupied by a single guanine whereas in the mutant gene, nt 57 is occupied by two guanines. This nucleotide position in exon 2 corresponds to nucleotide position 1036 in the normal glucocerebrosidase gene sequence in SEQ ID NO 1. The corresponding position in the cDNA from which the intervening sequences have been spliced is nucleotide position 84. The mutation is thus referred to by either its genomic position or by its cDNA position, the latter of which is designated by 84GG. The guanine nucleotide insertion alters the reading frame of the DNA and, despite the production of a normal amount of mRNA, results in total loss of glucocerebrosidase activity as the frame shift produces early termination. This Gaucher disease mutation was found in patients with the 1226/? Pv1.1./Pv1.1+ genotype. In Beutler's study of 72 Jewish subjects with Gaucher disease, screening for the 1226, 1448 and 84GG mutations accounted for 94.4% of the Gaucher producing alleles in the patient population.

Three clinical subtypes of Gaucher Disease have been delineated. See, Beutler, *Blood Rev.*, 2:59-70 (1988); Martin et al., *Adv. Pediatr.*, 36:277-306 (1989). Type I is by far the most common; more than 99% of Gaucher disease patients have Type I disease. It is defined by the fact that there is no neurologic involvement. Type II disease is a fulminating disorder with severe neurologic manifestations and death within the first 18 months of life. Type III, the juvenile form of the disorder is characterized by later onset of neurologic symptoms than Type II disease and by a chronic course.

Although all body cells are deficient in glucocerebrosidase activity in Gaucher disease, it is the glycolipid engorged macrophages that are responsible for all of the non-neurologic disease manifestation. The liver and spleen are usually enlarged. Splenomegaly results in or contributes to thrombocytopenia. Hepatic involvement is often associated with fibrosis and with abnormal liver function tests. In some patients right-to-left pulmonary shunting occurs, presumably secondary to the liver disease. Direct involvement of the pulmonary parenchyma may also rarely occur. Schneider et al., *Am. J. Med.*, 63:475-480 (1977).

Bone involvement is common in Gaucher disease. Flaring of the distal femur, the so-called Erlenmeyer flask deformity, is a classical sign of the disease. Aseptic necrosis of the femoral heads, bone infarcts, and pathologic fractures of the long bone are all frequent complications of Gaucher disease. Stowens et al., *Medicine*, 64:310-322 (1985). Bone crises Yosipovitch et al., *Isr. J. Med. Sci.*, 26:593-595 (1990), episodes of pain and swelling, sometimes accompanied by fever but without X-ray changes, are common recurrent manifestations of the disease.

There are patients with Type I disease who experience minimal manifestations of the disorder or none at all. Often the diagnosis in patients with such very mild disease is made in middle or old age. The presence of Gaucher disease in such patients is often appreciated only when bone marrow examination is performed for some unrelated disorder or in the course of investigation of modest thrombocytopenia. On more careful examination slight splenomegaly is often detected and minimal stigmata of the disease may be apparent when skeletal X-rays are examined. Such patients usually need no treatment.

In Type II disease, neurologic findings usually become manifest in the middle of the first year of life with the development of oculomotor apraxia, strabismus, hypertonicity and retroflexion of the head. Similar neurologic symptoms occurring in the first few years of life and occasionally even later characterize Type III disease.

Determination of leukocyte $\beta$-glucosidase activity is a reliable and simple way to diagnose Gaucher disease. Unfortunately, most patients with the disorder are still diagnosed by bone marrow examination. While this is understandable if the diagnosis was not suspected, it is an inappropriate and anachronistic procedure when Gaucher disease has been included in the differential diagnosis. Beutler and Savin, *Blood*, 76:646-648 (1990). Ancillary tests that are useful include the determination of the activity of serum acid phosphatase (Robinson et al., *Clin. Chem.*, 26:371-382 (1980)) and the angiotensin converting enzyme. Lieberman et al., *N. Enol. J. Med.*, 294:1442-1444 (1976). The levels of these enzymes, as well as levels of a number of lysosomal enzymes that are not usually measured in clinical laboratories, is increased in most but not all patients with Gaucher disease.

Recently, facile technology for the detection of the common mutations, such as those at cDNA nucleotide position 1226 (Beutler et al., *Clin. Chim. Acta.*, 194:161-166 (1990)), at cDNA nucleotide position 1448 (Zimran et al., *Lancet*, 2:349-352 (1989)) and at cDNA nucleotide position 84GG (Beutler et al., *Proc. Natl. Acad. Sci., USA*, 88:10544-10547 (1991) have been developed using the polymerase chain reaction (PCR).

BRIEF SUMMARY OF THE INVENTION

The present invention relates to detecting a new Gaucher disease mutation which is characterized by a point mutation of an adenine nucleotide substituted for a guanine nucleotide at nucleotide position 1 in intron 2 (also referred to as intervening sequence 2 (IVS2+1)) of the glucocerebrosidase gene. This intron 2 nucleotide position of the point mutation corresponds to nucleotide position 1068 of the glucocerebrosidase gene as shown in SEQ ID NO 1.

Thus, in one embodiment, a human genetic screening method is contemplated. The method comprises assaying a nucleic acid sample isolated from a human for the presence of a glucocerebrosidase gene point mutation characterized as a substitution of an adenine nucleotide for a guanine nucleotide at nucleotide position 1 of glucocerebrosidase gene intron 2.

In a preferred embodiment, the method comprises treating, under amplification conditions, a sample of genomic DNA from a human with a polymerase chain reaction (PCR) primer pair for amplifying a region of human genomic DNA containing nucleotide position 1 of glucocerebrosidase gene intron 2. The PCR treatment produces an amplification product containing the region, which is then assayed for the presence of a adenine nucleotide point mutation.

One object of the present invention is to provide a method for screening for at least two, and preferably three to four, glucocerebrosidase gene mutations in a single nucleic acid sample. Such multiple screening is most advantageously performed by producing two PCR amplification products, one containing genomic DNA exon 2 nucleotide position 57 and intron 2 nucleotide position 1, and one containing exon 9 nucleotide position 2 and exon 10 nucleotide position 60 in one PCR amplification step. Thus, primers for amplifying (1) a region of genomic DNA containing nucleotide position 1 of glucocerebrosidase gene intron 2 and nucleotide position 57 of glucocerebrosidase gene exon 2, and (2) a region of genomic DNA containing nucleotide position 2 of exon 9 and nucleotide position 60 of exon 10. The PCR amplification products are then assayed for the intron 2 nucleotide G→A, exon 2 nucleotide 57GG, exon 9 nucleotide 2 A G and exon 10 nucleotide 60 T→C mutations.

DETAILED DESCRIPTION OF THE INVENTION

A. Definitions

| TABLE OF CORRESPONDENCE | |
|---|---|
| Code Group | Nucleotide(s) |
| A A | adenine |
| C C | cytosine |
| G G | guanine |
| T T | thymine (in DNA) |
| U U | uracil (in RNA) |
| Y C or T(U) | pyrimidine |
| R A or G | purine |
| M A or C | amino |
| K G or T(U) | keto |
| S G or C | strong interaction (3 hydrogen bonds) |
| W A or T(U) | weak interaction (2 hydrogen bonds) |
| H A or C or T(U) | not-G |
| B G or T(U) or C | not-A |
| V G or C or A | not-T or not-U |
| D G or A or T(U) | not-C |
| N G,A,C or T(U) | any |

Allele: A variant of DNA sequence of a specific gene. In diploid cells a maximum of two alleles will be present, each in the same relative position or locus on homologous chromosomes of the chromosome set. When alleles at any one locus are identical the individual is said to be homozygous for that locus, when they differ the individual is said to be heterozygous for that locus. Since different alleles of any one gene may vary by only a single base, the possible number of alleles for any one gene is very large. When alleles differ, one is often dominant to the other, which is said to be recessive. Dominance is a property of the phenotype and does not imply inactivation of the recessive allele by the dominant. In numerous examples the normally functioning (wild-type) allele is dominant to all mutant alleles of more or less defective function. In such cases the general explanation is that one functional allele out of two is sufficient to produce enough active gene product to support normal development of the organism (i.e., there is normally a two-fold safety margin in quantity of gene product).

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: A double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it nonrandomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

DNA Homolog: A nucleic acid having a preselected conserved nucleotide sequence and a sequence coding for a receptor capable of binding a preselected ligand.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Stop Codon: Any of three codons that do not code for an amino acid, but instead cause termination of protein synthesis. They are UAG, UAA and UGA and are also referred to as a nonsense or termination codon.

Leader Polypeptide: A short length of amino acid sequence at the amino end of a protein, which carries or directs the protein through the inner membrane and so ensures its eventual secretion into the periplasmic space and perhaps beyond. The leader sequence peptide is commonly removed before the protein becomes active.

Reading Frame: Particular sequence of contiguous nucleotide triplets (codons) employed in translation. The reading frame depends on the location of the translation initiation codon.

B. Methods

The present invention provides a novel method for screening humans for glucocerebrosidase alleles associated with Gaucher's disease. The invention was based on the discovery that Gaucher disease can be caused by a point mutation (base substitution) in the glucocerebrosidase gene DNA sequence at nucleotide position 1 of intron 2 (also referred to as intervening sequence 2). The mutation sometimes referred to as IVS2+1. The nucleotide base substitution results in the deletion of exon 2 due to the loss of the intronic 5' donor site required for mRNA splicing. The transcript from the mutant gene, thus, also lacks exon 2 as a consequence of the absence of a guanine nucleotide in the 5' splice consensus. As a result of the loss of exon 2, functional glucocerebrosidase protein is not produced. In the glucocerebrosidase pseudogene, since an adenine nucleotide is normally found at this site, exon 2 is also lacking in the pseudogene transcript.

The DNA-based analysis for screening mutations in Gaucher disease-producing alleles resulted in the detection of the new mutation in intron 2 previously undetected. For this invention, DNA from 100 unrelated patients, 97 of whom were Jewish and three of whom were half-Jewish, was analyzed for 22 mutations known to cause Gaucher disease. All but seven of the alleles were identified as having previously described mutations. Five of the unidentified mutations proved to be a result of the IVS2+1 mutation.

The assay method can be used to diagnose either the disease itself or a heterozygous carrier state. Generally, the method involves preparing a nucleic acid sample for screening and then assaying the sample for one or more of the Gaucher disease alleles.

A glucocerebrosidase gene is a nucleic acid whose nucleotide sequence codes for glucocerebrosidase, mutant glucocerebrosidase, or glucocerebrosidase pseudogene. It can be in the form of genomic DNA, an mRNA or cDNA, and in single or double stranded form. Preferably, genomic DNA is used because of its relative stability in biological samples compared to mRNA. The sense strand of the complete genomic sequence of the normal (wild type) glucocerebrosidase gene is listed in the Sequence Listing as SEQ ID NO 1. The gene is comprised of eleven exons and ten introns, the nucleotide positions of which are indicated in the features of SEQ ID NO 1.

The nucleic acid sample is obtained from cells, typically peripheral blood leukocytes. Where mRNA is used, the cells will be lysed under RNase inhibiting conditions. In one embodiment, the first step is to isolate the total cellular mRNA. Poly A+ mRNA can then be selected by hybridization to an oligo-dT cellulose column.

In preferred embodiments, the nucleic acid sample is enriched for a presence of glucocerebrosidase allelic material. Enrichment is typically accomplished by subjecting the genomic DNA or mRNA to a primer extension reaction employing a polynucleotide synthesis primer as described herein. Particularly preferred methods for producing a sample to be assayed use preselected polynucleotides as primers in a polymerase chain reaction (PCR) to form an amplified (PCR) product.

(1) Preparation of Polynucleotide Primers

The term "polynucleotide" as used herein in reference to primers, probes and nucleic acid fragments or segments to be synthesized by primer extension is defined as a molecule comprised of two or more deoxyribonucleotides or ribonucleotides, preferably more than three. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057-70 (1984); Studier et al., *J. Mol. Biol.*, 189:113-130 (1986); and *Molecular Cloning: A Laboratory Manual*, Second Edition, Maniatis et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197-1202 1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719-736 (1974).

The polynucleotide primers can be prepared using any suitable method, such as, for example, the phosphotriester or phosphodiester methods see Narang et al., *Meth. Enzymol.*, 68:90, (1979); U.S. Pat. Nos. 4,356,270, 4,458,066, 4,416,988, 4,293,652; and Brown et al., *Meth. Enzymol.*, 68:109, (1979).

The choice of a primer's nucleotide sequence depends on factors such as the distance on the nucleic acid from the hybridization point to the region coding for the mutation to be detected, its hybridization site on the nucleic acid relative to any second primer to be used, and the like.

If the nucleic acid sample is to be enriched for glucocerebrosidase gene material by PCR amplification, two primers, i.e., a PCR primer pair, must be used for each coding strand of nucleic acid to be amplified. The first primer becomes part of the non-coding (anti-sense or minus or complementary) strand and hybridizes to a nucleotide sequence on the plus or coding strand. Second primers become part of the coding (sense or plus) strand and hybridize to a nucleotide sequence on the minus or non-coding strand. One or both of the first and second primers can contain a nucleotide sequence defining an endonuclease recognition site. The site can be heterologous to the glucocerebrosidase gene being amplified.

In one embodiment, the present invention utilizes a set of polynucleotides that form primers having a priming region located at the 3'-terminus of the primer. The priming region is typically the 3'-most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'-terminal (5'-most) non-priming portion, i.e., a region that does not participate in hybridization to the preferred template.

In PCR, each primer works in combination with a second primer to amplify a target nucleic acid sequence. The choice of PCR primer pairs for use in PCR is governed by considerations as discussed herein for producing glucocerebrosidase gene regions. When a primer sequence is chosen to hybridize (anneal) to a target sequence within a glucocerebrosidase gene allele intron, the target sequence should be conserved among the alleles in order to insure generation of target sequence to be assayed. Useful priming sequences are shown in Table 2 and also in Examples 3 and 4.

(2) Polymerase Chain Reaction

Glucocerebrosidase genes are comprised of polynucleotide coding strands, such as mRNA and/or the sense strand of genomic DNA. If the genetic material to be assayed is in the form of double stranded genomic DNA, it is usually first denatured, typically by melting, into single strands. The nucleic acid is subjected to a PCR reaction by treating (contacting) the sample with a PCR primer pair, each member of the pair having a preselected nucleotide sequence. The PCR primer pair is capable of initiating primer extension reactions by hybridizing to nucleotide sequences, preferably at least about 10 nucleotides in length, more preferably at least about 20 nucleotides in length and most preferably 17 nucleotides in length, conserved within the glucocerebrosidase alleles. The first primer of a PCR primer pair is sometimes referred to herein as the "anti-sense primer" because it hybridizes to a non-coding or anti-sense strand of a nucleic acid, i.e., a strand complementary to a coding strand. The second primer of a PCR primer pair is sometimes referred to herein as the "sense primer" because it hybridizes to the coding or sense strand of a nucleic acid.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR reaction product, thereby enriching the sample to be assayed for glucocerebrosidase genetic material.

PCR is typically carried out by thermocycling i.e., repeatedly increasing and decreasing the temperature of a PCR reaction admixture within a temperature range whose lower limit is about 30 degrees Celsius (30° C.) to about 55° C. and whose upper limit is about 90° C. to about 100°·C. The increasing and decreasing can be continuous, but is preferably phasic with time periods of relative temperature stability at each of temperatures favoring polynucleotide synthesis, denaturation and hybridization.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined for assaying for mutations.

The PCR reaction is performed using any suitable method. Generally it occurs in a buffered aqueous solution, i.e., a PCR buffer, preferably at a pH of 7-9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C. -100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. The thermocycling is repeated until the desired amount of PCR product is produced. An exemplary PCR buffer comprises the following: 50 mM KCl; 10 mM Tris-HCl at pH 8.3; 1.5 mM $MgCl_2$; 0.001% (wt/vol) gelatin, 200 $\mu$M dATP; 200 $\mu$M dTTP; 200 $\mu$M dCTP; 200 $\mu$M dGTP; and 2.5 units Thermus aquaticus (Taq) DNA polymerase I (U.S. Pat. No. 4,889,818) per 100 microliters ($\mu$) of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn-over rate of the RNA polymerase amplifies the starting polynucleotide as has been described by Chamberlin et al., *The Enzymes*, ed. P. Boyer, pp. 87-108, Academic Press, New York (1982). Amplification systems based on transcription have been described by Gingeras et al., in *PCR Protocols, A Guide to Methods and Applications*, pp. 245-252, Innis et al., eds, Academic Press, Inc., San Diego, Calif. (1990).

If the inducing agent is a DNA-dependent RNA polymerase and, therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

The PCR reaction can advantageously be used to incorporate into the product a preselected restriction site useful in detecting a mutation in the glucocerebrosidase gene.

PCR amplification methods are described in detail in U.S. Pat. Nos. 4,683,192, 4,683,202, 4,800,159, and 4,965,188, and at least in several texts including *PCR Technology: Principles and Applications for DNA Amplification*, H. Erlich, ed., Stockton Press, New York (1989); and *PCR Protocols: A Guide to Methods and Applications*, Innis et al., eds., Academic Press, San Diego, Calif. (1990).

In preferred embodiments, two pairs of first and second primers are used per amplification reaction. The amplification reaction products obtained from a plurality of different amplifications, each using a plurality of different primer pairs, can be combined or assayed separately.

However, the present invention also contemplates amplification using only one pair of first and second primers, and multiplex amplification (using up to about 8, 9 or 10 primer pairs).

(3) Nucleic Acid Sequence Analysis

Nucleic acid sequence analysis is approached by a combination of (a) physiochemical techniques, based on the hybridization or denaturation of a probe strand plus its complementary target, and (b) enzymatic reactions with endonucleases, ligases, and polymerases. Nucleic acid can be assayed at the DNA or RNA level. The former analyzes the genetic potential of individual humans and the latter the expressed information of particular cells.

In assays using nucleic acid hybridization, detecting the presence of a DNA duplex in a process of the present invention can be accomplished by a variety of means.

In one approach for detecting the presence of a DNA duplex, an oligonucleotide that is hybridized in the DNA duplex includes a label or indicating group that will render the duplex detectable. Typically such labels include radioactive atoms, chemically modified nucleotide bases, and the like.

The oligonucleotide can be labeled, i.e., operatively linked to an indicating means or group, and used to detect the presence of a specific nucleotide sequence in a target template.

Radioactive elements operatively linked to or present as part of an oligonucleotide probe (labeled oligonucleotide) provide a useful means to facilitate the detection of a DNA duplex. A typical radioactive element is one that produces beta ray emissions. Elements that emit beta rays, such as $^3H$, $^{12}C$, $^{32}P$ and $^{35}S$ represent a class of beta ray emission-producing radioactive element labels. A radioactive polynucleotide probe is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate-forming compound such as an EDTA-analogue so that a fluorescent lanthanide complex is formed. See U.S. Pat. Nos. 4,374,120, 4,569,790 and published Patent Application EP0139675 and W087/02708.

Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligonucleotide, such as non-hybridized labeled oligonucleotide probe, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is $^{32}$P. Southern, *J. Mol. Biol.*, 98:503 (1975).

The oligonucleotides can also be advantageously linked, typically at or near their 5'-terminus, to a solid matrix, i.e., aqueous insoluble solid support. Useful solid matrices are well known in the art and include cross-linked dextran such as that available under the tradename SEPHADEX from Pharmacia Fine Chemicals (Piscataway, N.J.); agarose, polystyrene or latex beads about 1 micron to about 5 millimeters in diameter, polyvinyl chloride, polystyrene, cross-linked polyacrylamide, nitrocellulose or nylon-based webs such as sheets, strips, paddles, plates microtiter plate wells and the like.

It is also possible to add "linking" nucleotides to the 5' or 3' end of the member oligonucleotide, and use the linking oligonucleotide to operatively link the member to the solid support.

In nucleotide hybridizing assays, the hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 4° C. to 37° C., preferably about 12° C. to about 30° C., more preferably about 22° C., and for time periods from 0.5 seconds to 24 hours, preferably 2 minutes (min) to 1 hour. Exemplary are the conditions described in Example 4.

Hybridization can be carried out in a homogeneous or heterogeneous format as is well known. The homogeneous hybridization reaction occurs entirely in solution, in which both the oligonucleotide and the nucleic acid sequences to be hybridized (target) are present in soluble forms in solution. A heterogeneous reaction involves the use of a matrix that is insoluble in the reaction medium to which either the oligonucleotide, polynucleotide probe or target nucleic acid is bound.

Where the nucleic acid containing a target sequence is in a double stranded (ds) form, it is preferred to first denature the dsDNA, as by heating or alkali treatment, prior to conducting the hybridization reaction. The denaturation of the dsDNA can be carried out prior to admixture with a oligonucleotide to be hybridized, or can be carried out after the admixture of the dsDNA with the oligonucleotide.

Predetermined complementarity between the oligonucleotide and the template is achieved in two alternative manners. A sequence in the template DNA may be known, such as where the primer to be formed can hybridize to known glucocerebrosidase sequences and can initiate primer extension into a region of DNA for sequencing purposes, as well as subsequent assaying purposes as described herein, or where previous sequencing has determined a region of nucleotide sequence and the primer is designed to extend from the recently sequenced region into a region of unknown sequence. This latter process has been referred to a "directed sequencing" because each round of sequencing is directed by a primer designed based on the previously determined sequence.

Effective amounts of the oligonucleotide present in the hybridization reaction admixture are generally well known and are typically expressed in terms of molar ratios between the oligonucleotide to be hybridized and the template. Preferred ratios are hybridization reaction mixtures containing equimolar amounts of the target sequence and the oligonucleotide. As is well known, deviations from equal molarity will produce hybridization reaction products, although at lower efficiency. Thus, although ratios where one component can be in as much as 100 fold molar excess relative to the other component, excesses of less than 50 fold, preferably less than 10 fold, and more preferably less than two fold are desirable in practicing the invention.

(a) Detection of Membrane-Immobilized Target Sequences

In the DNA (Southern) blot technique, DNA is prepared by PCR amplification as previously discussed. The PCR products (DNA fragments) are separated according to size in an agarose gel and transferred (blotted) onto a nitrocellulose or nylon membrane. Conventional electrophoresis separates fragments ranging from 100 to 30,000 base pairs while pulsed field gel electrophoresis resolves fragments up to 20 million base pairs in length. The location on the membrane a containing particular PCR product is determined by hybridization with a specific, labeled nucleic acid probe.

In preferred embodiments, PCR products are directly immobilized onto a solid-matrix (nitrocellulose membrane) using a dot-blot (slot-blot) apparatus, and analyzed by probe-hybridization. See U.S. Patents Nos. 4,582,789 and 4,617,261.

Immobilized DNA sequences may be analyzed by probing with allele-specific oligonucleotide (ASO) probes, which are synthetic DNA oligomers of approximately 20 nucleotides, preferably 17 nucleotides in length. These probes are long enough to represent unique sequences in the genome, but sufficiently short to be destabilized by an internal mismatch in their hybridization to a target molecule. Thus, any sequences differing at single nucleotides may be distinguished by the different denaturation behaviors of hybrids between the ASO probe and normal or mutant targets under carefully controlled hybridization conditions.

(b) Detection of Target Sequences in Solution

Several rapid techniques that do not require nucleic acid purification or immobilization have been developed. For example, probe/target hybrids may be selectively isolated on a solid matrix, such as hydroxylapatite, which preferentially binds double-stranded nucleic acids. Alternatively, probe nucleic acids may be immobilized on a solid support and used to capture target sequences from solution. Detection of the target sequences can be accomplished with the aid of a second, labeled probe that is either displaced from the support by the target sequence in a competition-type assay or joined to the support via the bridging action of the target sequence in a sandwich-type format.

In the oligonucleotide ligation assay (OLA), the enzyme DNA ligase is used to covalently join two synthetic oligonucleotide sequences selected so that they can base pair with a target sequence in exact head-to-tail juxtaposition. Ligation of the two oligomers is prevented by the presence of mismatched nucleotides at the junction region. This procedure allows for the distinction between known sequence variants in samples of cells without the need for DNA purification. The joint of the two oligonucleotides may be monitored by immobilizing one of the two oligonucleotides and observing whether the second, labeled oligonucleotide is also captured.

(c) Scanning Techniques for Detection of Base Substitutions

Three techniques permit the analysis of probe/target duplexes several hundred base pairs in length for unknown single-nucleotide substitutions or other sequence differences. In the ribonuclease (RNase) A technique, the enzyme cleaves a labeled RNA probe at positions where it is mismatched to a target RNA or DNA sequence. The fragments may be separated according to size allowing for the determination of the approximate position of the mutation. See U.S. Pat. No. 4,946,773.

In the denaturing gradient gel technique, a probe-target DNA duplex is analyzed by electrophoresis in a denaturing gradient of increasing strength. Denaturation is accompanied by a decrease in migration rate. A duplex with a mismatched base pair denatures more rapidly than a perfectly matched duplex.

A third method relies on chemical cleavage of mismatched base pairs. A mismatch between T and C, G, or T, as well as mismatches between C and T, A, or C, can be detected in heteroduplexes. Reaction with osmium tetroxide (T and C mismatches) or hydroxylamine (C mismatches) followed by treatment with piperidine cleaves the probe at the appropriate mismatch.

(4) Preferred Embodiments

In view of the foregoing, the present invention contemplates a screening method comprising treating, under amplification conditions, a sample of genomic DNA isolated from a human with a PCR primer pair for amplifying a region of human genomic DNA containing nucleotide (nt) position 1 of glucocerebrosidase intron 2, also referred to as IVS2+1. Amplification conditions include, in an amount effective for DNA synthesis, the presence of PCR buffer and a thermocycling temperature. The PCR product thus produced is then assayed for the presence of an adenine nucleotide point mutation at nt position 1 of intron 2. Preferably, the PCR product contains a continuous nucleotide sequence comprising 358 base pairs (bp) written from 5' to 3' direction represented by the formula:

5'-GAATGTCCCAAGCCTTTGAGTAGG-GTAAGCATCATGGCTGGCAGCCTCACA GGATTGCTTCTACTTCAGGCAGTGTCGTGG-GCATCAGATGAGTGAGTCAAGGCA GTGGGGAGGTAG-CACAGAGCCTCCCTTCTGCCT-CATAGTCCTTTGGTAGCCTTC CAG-TAAGCTGGTGGTAGACTTTTAGTAGGTGCT-CAATAAATCCTTTTGAGTGAC TGAGAC-CAACTTTGGGGTGAG-GATTTTGTTTTTTTTCTTTT-GAAACAGAGTCTT ACTCTGTTGCCTGGGCT-GGAGTGCAGTGGTGCAATTTTGGCTCATT-CCAACCTC TGCCTCCCAGATTCAAGC-GATTCTCTTGCTTCAGCTT-3' (SEQ ID NO 2).

Preferably, the PCR primer pair used in amplifying regions of the glucocerebrosidase gene comprises a first primer that hybridizes to an anti-sense strand of the exon 2 at a location 5' to nucleotide 88 of the exon, and a second primer that hybridizes to a sense strand of the intron 2 at a location 3' to nucleotide 1 of the intron. A preferred first primer is represented by the formula, 5'-GAATGTCCCAAGCCTTTGA-3' (SEQ ID NO 3), and a preferred second primer is represented by the formula, 5'-AAGCTGAAGCAAGAGAATCG-3' (SEQ ID NO 4).

In one preferred embodiment, the PCR product is assayed for the IVS2+1 mutation by treating the amplification product, under hybridization conditions, with an oligonucleotide probe specific for the IVS2+1 mutation, and detecting the formation of any hybridization product. A preferred oligonucleotide probe contains a nucleotide sequence represented by the formula, 5'-GGCATCAGATGAGTGAG-3' (SEQ ID NO 5). Oligonucleotide hybridization to target nucleic acid is described in U.S. Pat. No. 4,530,901.

In another preferred embodiment, PCR primer pair produces an amplification product that contains a preselected Hph I restriction enzyme site if the IVS2+1 mutation is absent. The Hph I restriction enzyme cleaves at the asterisk-marked position on the double stranded DNA sequence represented by the formula shown below:

5'-GGTGA(N)₈*-3' (SEQ ID NO 6)
3'-CCTCT(N)₇*-5' (SEQ ID NO 7)
where N can be A, C, G or T.

A preferred first primer for amplifying the product containing the Hph I restriction site is represented by the formula, 5'-GAATGTCCCAAGCCTTTGA-3' (SEQ ID NO 3) and a preferred second primer is represented by the formula, 5'-AAGCTGAAG-CAAGAGAATCG-3' (SEQ ID NO 4). Preferably, the PCR product contains a continuous nucleotide sequence comprising 358 bp written from 5' to 3' direction represented by the formula shown in SEQ ID NO 2.

Assaying comprises treating, under restriction conditions, the amplification product with the Hph I restriction enzyme that recognizes the sequence listed as SEQ ID NOs 6 and 7 site, and detecting the presence of restriction products. As described in Example 3, if the amplification product does not contain the IVS2+1 mutation, the resultant Hph I restriction enzyme cuts at the natural Hph I site at the end of exon 2 and the beginning of intron 2 (nucleotide positions 1067-1071 in SEQ ID NO 1). The resultant digestion product contains three fragments of 141, 117 and 100 bp in length. If the amplification product is from a mutant allele containing the IVS2+1 mutation of an adenine in place of a guanine nucleotide, the resultant Hph I restriction enzyme will not cut at the site created in the exon 2-intron 2 junction. The resultant digestion product of a normal allele thus contains two fragments of 241 and 117 bp in length.

Also contemplated is a screening method for detection of multiple glucocerebroside mutations IVS2+1, exon 2 nt 57G (84GG), exon 9 nt 2G (1226G) and exon 10 nt 60 C (1448C) wherein a PCR admixture is formed by combining, in a PCR buffer, a sample of genomic DNA and two glucocerebrosidase gene-specific primer pairs each set of which is defined by 5' and 3' primers. The 5' primer in the first set is capable of priming within a region of human genomic DNA corresponding to nucleotide positions 1-57 of glucocerebroside gene. The first 3' primer is capable of priming within a region of human genomic DNA 3' to nucleotide position 1 of intron 2, preferably corresponding to nucleotide positions 251-270 of glucocerebroside gene intron 2. The 5' primer in the second set is capable of priming within a region of human genomic DNA corresponding to nucleotide positions 841-860 of glucocerebroside gene intron 7. The second 3' primer is capable of priming within a region of human genomic DNA corresponding to nucleotide positions 26-45 of glucocerebroside gene intron 10.

The PCR admixture thus formed is subjected to a plurality of PCR thermocycles to produce glucocerebroside gene amplification products. The amplification products are then treated, under hybridization conditions, with an oligonucleotide probe specific for each mutation. Any hybridization products are then detected. A preferred first 5' primer is represented by the formula, 5'-GAATGTCCCAAGCCTTTGA-3' (SEQ ID NO 3), and a first 3' primer is represented by the formula, 5'-AAGCTGAAGCAAGAGAATCG-3' (SEQ ID NO 4). A preferred second 5' primer is represented by the formula, 5'-CAAGGTCCAGGAT-CAGTTGC-3' (SEQ ID NO 8) and a preferred second 3' primer is represented by the formula, 5'-AACGCTGTCTTCAGCCCACT-3' (SEQ ID NO 9).

Amplification products are assayed with both a probe or probes specific for a mutation and a corresponding probe or probes specific for the normal gene sequence. Preferred probes for hybridizing to the glucocerebroside gene mutations IVS2+1, exon 2 nt 57G (84GG), exon 9 nt 2G (1226G) and exon 10 nt 60 C (1448C) have the respective nucleotide sequences represented by SEQ ID NO 5, SEQ ID NO 12, SEQ ID NO 14 and SEQ ID NO 16.

C. Primers and Probes

The present invention further contemplates polynucleotide synthesis primers have nucleotide sequences represented by SEQ ID NO 3, SEQ ID NO 4, SEQ ID NO 8, and SEQ ID NO 9.

Also contemplated are oligonucleotide probes having nucleotide sequences represented by SEQ ID NO 5, SEQ ID NO 10, SEQ ID NO 11, SEQ ID NO 12, SEQ ID NO 13, SEQ ID NO 14, SEQ ID NO 15 and SEQ ID NO 16.

EXAMPLES

The following examples are intended to illustrate but are not to be construed as limiting of the specification and claims in any way.

Preparation and Preliminary Screening of Genomic DNA

High molecular weight DNA was extracted from the white blood cells from a 100 unrelated patients, 97 of whom were Jewish and three of whom were half-Jewish. For the initial screening of genomic DNA, blood was collected after informed consent from the patients described above and anticoagulated with a mixture of 0.14M citric acid, 0.2M trisodium citrate, and 0.22M dextrose. The anticoagulated blood was centrifuged at 800 x g for 15 minutes at room temperature and the platelet-rich plasma supernatant was discarded. The pelleted erythrocytes, mononuclear and polynuclear cells were resuspended and diluted with a volume equal to the starting blood volume with chilled 0.14M phosphate buffered saline (PBS), pH 7.4. The peripheral blood white blood cells were recovered from the diluted cell suspension by centrifugation on low endotoxin Ficoll-Hypaque (Sigma Chem. Corp. St. Louis, Mo.) at 400 x g for 10 minutes at 18 degrees C. (18° C.). The pelleted white blood cells were then resuspended and used for the source of high molecular weight DNA.

The high molecular weight DNA was purified from the isolated white blood cells using methods well known to one skilled in the art and described by Maniatis et al., *Molecular Cloning: A Laboratory Manual*, 2nd ed. Cold Spring Harbor Laboratory, Sections 9.16-9.23, (1989) and U.S. Pat. No. 4,683,195. All samples were first screened for the presence of a restriction polymorphism with the restriction enzyme Pvu II as the glucocerebrosidase genotype is also sometimes characterized by this polymorphism which exists in intron 6 of the glucocerebrosidase gene. See, Zimran et al., *Am. J. Hum. Genet.*, 46:902-905 (1990). Briefly, the Pvu II polymorphism was assayed by PCR amplification, as described in Example 3, of intron 6 of glucocerebrosidase genomic DNA followed by restriction digestion with Pvu II restriction endonuclease (New England Biolabs, Beverly, Mass.). The 5' anti-sense oligonucleotide primer corresponding to a region in exon 6 used in amplifying intron 6 had the sequence 5'-TCAAGAC-CAATGGAGCGGTG-3' (SEQ ID NO 17). The 3' sense oligonucleotide primer corresponding to a region in exon 7 had the sequence 5'-CTAGGTCACGG-GCAATGAAG-3' (SEQ ID NO 18). The resultant PCR amplified product was 794 base pairs in length. The Pvu II polymorphic site is a G→A single-base substitution at nucleotide position 3938 of the normal glucocerebrosidase gene sequence shown in SEQ ID NO 1. Thus, the normal gene lacks the restriction site and is designated as the "+" allele while the mutant gene has the restriction site and is designated as the "−" allele. Alleles containing this polymorphism were designated as Each sample of DNA was then examined as described in Example 3 and 4 for the point mutation of a guanine nucleotide for an adenine nucleotide at the 1226 nucleotide position of the glucocerebrosidase cDNA. This mutation will hereinafter be referred to by its exon location at nucleotide position 2 in exon 9 of the glucocerebrosidase gene. This mutation was invariably found in the context (i.e., linked to) of the Pv1.1 genotype. See Zimran et al., supra, (1990). DNA from individuals who were homozygous for the mutation, thus having the Pv1.1/Pv1.1 polymorphism on both alleles, was not examined further. The diagnosis of Gaucher disease was well-established in all patients, either by histopathologic study of the marrow or demonstration of diagnostically lowered levels of acid beta-glucosidase in peripheral blood cells. Classification by ethnic origin was according to the family history provided by each patient. Genomic DNA samples determined to be heterozygous were further analyzed for the presence of the insertion mutation in exon 2 at nucleotide (nt) 57 (also referred to as 84GG corresponding to the cDNA position) and for the point mutation in exon 10 at nt position 60 (also referred to as 1448C corresponding to the cDNA position). Unidentified Gaucher disease alleles were designated as "?". For patients having mutations not identified by the preliminary screening, the corresponding cDNAs were analyzed as described in Example 2.

2. Preparation and Sequencing of cDNA

Total cellular RNA was purified from cultured lymphoblasts or fibroblasts from the patients having the 1226G/? Pv1.1/Pv1.1+ genotype. The purification procedure was performed as described by Chomczynski et al., *Anal. Biochem.*, 162:156-159 (1987). Briefly, the cells were prepared as described in Example 1. The cells were then homogenized in 10 milliliters (ml) of a denaturing solution containing 4.0M guanidine thiocyanate, 0.1M Tris-HCl at pH 7.5, and 0.1M beta-mercaptoethanol to form a cell lysate. Sodium lauryl sarcosinate was then admixed to a final concentration of 0.5% to the cell lysate after which the admixture was centrifuged at 5000 X g for 10 minutes at room temperature. The resultant supernatant containing the total RNA was layered onto a cushion of 5.7M cesium chloride and 0.01M EDTA at pH 7.5 and was pelleted by centrifugation. The resultant RNA pellet was dissolved in a solution of 10 mM Tris-HCl at pH 7.6 and 1 mM EDTA (TE) containing 0.1% sodium docecyl sulfate (SDS). After phenolchloroform extraction and ethanol precipitation, the purified total cellular RNA concentration was estimated by measuring the optical density at 260 nm.

Total RNA prepared above was used as a template for cDNA synthesis using reverse transcriptase for first strand synthesis and PCR with oligonucleotide primers designed so as to amplify the cDNA in two overlapping fragments designated the 5' and the 3' fragment. The oligonucleotides used in practicing this invention were synthesized on an Applied Biosystems 381A DNA Synthesizer following the manufacturer's instructions. To create the 5' fragment, first strand synthesis was performed using a sense primer (defined as hybridizing to the sense or coding template strand and priming the synthesis of the non-coding strand as described in the detailed description section of the specification) corresponding to the region in the glucocerebrosidase cDNA beginning at nucleotide 1298 and extending through nucleotide 1317. In a typical 50 microliters ($\mu$l) transcription reaction, 2 to 4 micrograms ($\mu$g) RNA prepared above and diluted in water was first annealed with 250 nanograms (ng) of the 3' sense oligonucleotide primer having the nucleotide sequence 5'-ACTGTCGACAAAGTTACGCA-3' (SEQ ID NO 19) at 65° C. for five minutes. The 3' primer corresponded to nucleotide positions 74 through 93 of glucocerebrosidase exon 9 (nt 5926–5945 in SEQ ID NO 1). Subsequently, 12 $\mu$l of the first strand cDNA synthesis reaction admixture was admixed to a 20 $\mu$l system containing 1.0 mM each of dATP, dCTP, dGTP, and dTTP, 40 mM Tris-HCl at pH 8.0, 8 mM MgCl$_2$, 50 mM NaCl, 2 mM spermidine, 1 U of RNase block (Stratagene), and 25 U of AMV reverse transcriptase. The solution Was maintained for 1 hour at 42° C. and then five minutes at 65° C. to form first strand cDNA. Twenty $\mu$l of the first strand cDNA of the 5' fragment was then diluted with 80 $\mu$l of a PCR reaction admixture containing 250 ng of the 5' anti-sense oligonucleotide having the sequence 5' CTCTGGAACCCCTGTGGTCT-3' (SEQ ID NO 20) and 250 ng of the 3 sense oligonucleotide having the sequence 5'-GGGTCCTCCTTCGGGGTTCA-3' (SEQ ID NO 21) in a solution final concentration of 1.0 mM each of dATP, dCTP, dGTP, and dTTP, 40 mM Tris-HCl at pH 8.0, 8 mM MgCl$_2$, 50 mM NaCl, 2 mM spermidine, 5% DMSO and 3.5 U of Taq (Thermus aquaticus) DNA polymerase I (Boerhinger Mannheim, Indianapolis, Id.). The 5' primer corresponded to the nucleotide positions 184 through 203 of glucocerebrosidase exon 1 (nt 539–nt 558 in SEQ ID NO 1). The 3' primer corresponded to the nucleotide positions 47 through 66 of glucocerebrosidase exon 9 (nt 5899–nt 5918 in SEQ ID NO 1). The reaction mixture was overlaid with mineral oil and subjected to 35 cycles of amplification on a DNA Thermal Cycler (Perkin Elmer, South Plainfield, N.J. —Cetus, Emeryville, Calif.). Each amplification cycle included denaturation at 92° C. for 30 seconds, annealing at 58° C. for 30 minutes and elongation at 72° C. for 30 seconds. The amplified cDNA samples were then extracted twice with phenol/chloroform, once with chloroform, ethanol precipitated and are stored at −70° C. in water. The amplified cDNA was comprised of a portion of the leader sequence of the cDNA which corresponded to the 5' portion of exon 1 and extended through most of entire cDNA which corresponded to exon 9 of the genomic sequence. The length of the amplified cDNA 5' product was approximately 1336 base pairs.

For sequencing of the resultant amplified cDNA 5' fragment, single stranded DNA was first generated. Five to ten percent of the amplified cDNA products prepared above served as the template in a unbalanced PCR amplification where either a 5' anti-sense oligonucleotide primer having the sequence 5'-CTCTTCATC- TAATGACCCTG-3' (SEQ ID NO 22) or a 3' sense oligonucleotide primer having the sequence 5'-CTAGGTCACGGGCAATGAAG-3' (SEQ ID NO 23) was used. The 5' primer corresponded to nucleotide positions 205 through 224 of glucocerebrosidase gene exon 1 (nt 560-nt 579 in SEQ ID NO 1). The 3' primer corresponded to nucleotide positions 130 through 149 of glucocerebrosidase gene exon 7 (nt 4246-nt 4265 of SEQ ID NO 1). The PCR amplification was performed as described above with the exception of the different primers. Sequencing of the single stranded PCR-generated cDNA was accomplished with cDNA primers spaced approximately 200 nucleotides apart along the single stranded cDNA.

First strand synthesis for the 3' fragment of the glucocerebrosidase cDNA was performed as described above for the 5' fragment with the exception of using different oligonucleotide primers. A 3' sense primer having the nucleotide sequence 5'-GCTCCACGGGC-CCAGTTCTG-3' (SEQ ID NO 24) corresponding to the region in the glucocerebrosidase cDNA beginning at nucleotide 2011 and extending through nucleotide 2030 was used in the transcription reaction. The 3' primer corresponded to nucleotide positions 507 through 526 of glucocerebrosidase exon 11 (nt 7102-nt 7121 in SEQ ID NO 1).

Twenty μl of the first strand cDNA of the 3' fragment was then diluted with 80 μl of a PCR reaction admixture containing 250 ng of the 5' anti-sense oligonucleotide having the sequence 5'-CATCATCCGG-GTACCCATGG-3' (SEQ ID NO 25) and 250 ng of the 3' sense oligonucleotide having the sequence 5'-ATGGGGGCTGGGGGGACACT-3' (SEQ ID NO 26) in a solution final concentration of 1.0 mM each of dATP, dCTP, dGTP, and dTTP, 40 mM Tris-HCl at pH 8.0, 8 mM MgCl₂, 50 mM NaCl, 2 mM spermidine, 5% DMSO and 3.5 U of Taq polymerase (Boehringer Mannheim). The 5' primer corresponded to the nucleotide positions 14 through 33 of glucocerebrosidase exon 5 (nt 3060-nt 3069 in SEQ ID NO 1). The 3' primer corresponded to the nucleotide positions 316 through 335 of glucocerebrosidase exon 11 (nt 6912-nt 6931 in SEQ ID NO 1). The reaction was performed as described above for the 5' fragment. The length of the amplified cDNA product was approximately 1372 base pairs.

For sequencing of the resultant amplified cDNA 3' fragment, single stranded DNA was first generated. Five to ten percent of the amplified cDNA products prepared above served as the template in a unbalanced PCR amplification where either a 5' anti-sense oligonucleotide primer having the sequence 5'-ACCCCTGAACATCAGCGAGA-3' (SEQ ID NO 27) or a 3' sense oligonucleotide primer having the sequence 5'-GCCCAGTGCCTCCTTGAGTA-3' (SEQ ID NO 28) was used. The 5' primer corresponded to nucleotide positions 110 through 129 of glucocerebrosidase gene exon 7 (nt 4226-nt 4245 in SEQ ID NO 1). The 3' primer corresponded to nucleotide positions 116 through 135 of glucocerebrosidase gene exon 11 (nt 6712-nt 6731 of SEQ ID NO 1). The PCR amplification was performed as described above with the exception of the different primers. Sequencing of the single stranded PCR-generated cDNA was accomplished with cDNA primers spaced approximately 200 nucleotides apart along the single stranded cDNA.

The sequences determined directly from the PCR-amplified cDNAs from the patients with Gaucher disease having the 1226G/? Pv1.1⁻/Pv1.1⁺ genotype revealed the absence of exon 2. To determine the nature of the mutation resulting in the deletion of exon 2, genomic DNA from those patients was first amplified and subjected to restriction digestion analysis and allele specific oligonucleotide hybridization as respectively described in Examples 3 and 4 below.

3. Preparation of PCR Amplified Genomic DNA Containing the IVS2+1 Point Mutation and Detection by Hph I Restriction Digestion The intron 2 point mutation (IVS2+1) was determined using two approaches. As described in this Example, the mutation was identified by amplifying genomic DNA by PCR followed by Hph I restriction endonuclease digestion. The detection of the mutation by amplifying genomic DNA by PCR followed by allele specific oligonucleotide hybridization is described below in Example 4.

For performing the restriction digestion analysis, a PCR primer pair was selected that produced an amplification product that contained a natural Hph I restriction enzyme site if the normal guanine nucleotide was present. Thus, the IVS2+1 mutation of an adenine nucleotide at that position was lacking. The Hph I restriction enzyme cleaved at the asterisk-marked position on the double stranded DNA sequence represented by the formula shown below:

5'-GGTGA(N)₈*-3' (SEQ ID NO 6)
3'-CCTCT(N)₇*-5' (SEQ ID NO 7)

where N can be A, C, G or T.

As shown herein, if the amplification product did not contain the IVS2+1 mutation, the resultant Hph I restriction enzyme recognized the natural Hph I site at the end of exon 2 and the beginning of intron 2 (nucleotide positions 1067-1071 in SEQ ID NO 1). The resultant digestion product contained three fragments of 141, 117 and 100 bp in length. If the amplification product was from a mutant allele containing the IVS2+1 mutation of an adenine nucleotide in place of a guanine nucleotide, the resultant Hph I restriction enzyme did not cut at the site created in the exon 2-intron 2 junction. The resultant digestion product of a normal allele thus contained two fragments of 241 and 117 bp in length.

As the pseudogene normally has an adenine residue at nucleotide position 1 of intron 2 instead of the guanine residue in the normal glucocerebrosidase gene, the primers for amplifying the region of DNA having the point mutation were designed so that only the functional glucocerebrosidase gene would be amplified and not the pseudogene. The 5' anti-sense oligonucleotide primer mismatched the pseudogene at two positions in exon 2 at nucleotide positions 17 and 19 and has the sequence 5'-GAATGTCCCAAGCCTTTGA-3' (SEQ ID NO 3). The 5' primer corresponded to the nucleotide positions 1 through 19 of glucocerebrosidase exon 2. The 3' sense oligonucleotide primer corresponding to the nucleotide positions 251 through 270 of glucocerebrosidase intron 2 has the sequence, 5'-AAGCT-GAAGCAAGAGAATCG-3' (SEQ ID NO 4).

PCR amplification to determine the presence or absence of the insertion mutation was performed on 0.5 μg of genomic DNA prepared in Example 1 in a 1X PCR buffer (20X PCR buffer consisted at final concentration 670 μl of 2M Tris-HCl at pH 8.8, 166 μl of 2M ammonium sulfate, 134 μl of 1M MgCl₂, 42.5 μl of an 80 mg/ml solution of bovine serum albumin and water up to 2 ml) containing 0.5 mM each of dATP, dGTP, dCTP and dTTP, 5% DMSO, 300 ng of each oligonucleotide primer described above and 3 U Taq DNA polymerase (Boehringer Mannheim). Twenty-eight amplification cycles of PCR were performed as described in Example 2 to form amplified genomic DNA products spanning exon 2 and a portion of intron 2 of the glucocerebrosidase gene (referred to as exon 2/intron 2). Each amplification cycle consisted of denaturation for 30 seconds at 92° C., annealing for 30 seconds at 59° C. and extending for 40 seconds at 72° C.

Fifteen μl of the amplified glucocerebrosidase exon 2/intron 2 products were then maintained in a 50 μl digestion system with 1X New England Biolabs Buffer Number 2 (New England Biolabs) and 20 U Hph I restriction endonuclease for 1.5 hours at 60° C. After admixture of 2.5 volumes of ethanol followed by chilling, the precipitate was dried, redissolved in 15 μl gel loading dye buffer and electrophoresed on a 12% acrylamide gel.

PCR amplified genomic DNA exon 2/intron 2 products having the point mutation of a G nucleotide in glucocerebrosidase intron 2 was cleaved into two fragments of 241 and 117 bp. The resultant PCR product of a mutant allele contained a continuous nucleotide sequence comprising 258 base pairs (bp) written from 5' to 3' direction represented by the formula shown in SEQ ID NO 2. The normal allele was cleaved in two locations resulting in three fragments of 141, 117 and 100 bp. Thus, PCR amplification followed by restriction digestion with Hph I of genomic DNA from heterozygous patients having the genotype described in Example 1 confirmed the presence of a point mutation in glucocerebrosidase intron 2 at nucleotide position .

4. Preparation of PCR Amplified Genomic DNA Containing the IVS2+1 Point Mutation and Detection by Allel Specific Oligonucleotide Hybridization The point mutation in glucocerebrosidase intron 2 at nucleotide position one was determined by an alternative approach in which PCR amplified genomic DNA containing the mutation was detected by hybridization with oligonucleotide probes that hybridized to that region. To amplify the intron 2 region having the point mutation for hybridization with oligonucleotide specific probes, PCR amplifications were performed as essentially described in Example 3 with 180 ng of each of the following primers. The 5' anti-sense oligonucleotide primer mismatched the pseudogene at two positions in exon 2 at nucleotide positions 17 and 19 and has the sequence 5'-GAATGTCCCAAGCCTTTGA-3' (SEQ ID NO 3). The 5' primer corresponded to the nucleotide positions 1 through 19 of glucocerebrosidase exon 2. The 3' sense oligonucleotide primer corresponded to a region 3' to nucleotide position 1 in intron 2 (nt 251–nt 270) and has the sequence, 5'-AAGCTGAAGCAAGAGAATCG-3' (SEQ ID NO 4). The resultant PCR product spanning from the beginning of exon 2 through a portion of intron 2 (referred to as exon 2/intron 2) contained a continuous nucleotide sequence of 358 bp written from 5' to 3' direction represented by the formula shown in SEQ ID NO 2.

Following the PCR amplification, 2 l of the amplified glucocerebrosidase exon 2/intron 2 DNA products were spotted onto separate sheets of nitrocellulose. After the spotted amplified DNA had dried, the nitrocellulose was treated with 0.5N NaOH for 2 minutes, 1M Tris-HCl at pH 7.5 for 2 minutes, followed by 0.5M Tris-HCl at pH 7.5 containing 1.5M NaCl for 2 minutes to denature and then neutralize the DNA. The resultant filters were baked under a vacuum for 1 hour at 80° C., were prehybridized for at least 20 minutes at 42° C. with a prehybridization solution consisting of 6X SSC (1X=0.15M NaCl, 0.15M sodium citrate), 5X Denhardt's solution (5X=0.1% polyvinylpyrrolidone, 0.1% ficoll, and 0.1% bovine serum albumin), 5 mM sodium phosphate buffer at pH 7.0, 0.5 mg/ml salmon testis DNA and 1% SDS.

After the prehybridization step, the nitrocellulose filters were separately exposed to $^{32}$P-labeled oligonucleotide probes diluted in prehybridization buffer. Labeling of the probes with $^{32}$P was performed by admixing 2.5 μl of 10X concentrate of kinase buffer (10X=0.5M Tris[hydroxymethyl] aminomethane hydrochloride (Tris-HCl) at pH 7.6, 0.1M MgCl$_2$, 50 mM dithiothreitol (DTT), 1 mM spermidine-HCl, and 1 mM ethylenediaminetetraacetic acid (EDTA)), 1.1 μl 1 60 μg/μl of a selected oligonucleotide, 18.4 μl water, 2 μl of 6000 Ci/mM of gamma $^{32}$P ATP at a concentration of 150 mCi/μl, and 1 μl of 10 U/μl polynucleotide kinase. The labeling admixture was maintained for 20 minutes at 37° C. followed by 2 minutes at 68° C. The maintained admixture was then applied to a Sephadex G50 (Pharmacia, Inc., Piscataway, NJ) spin column to remove unincorporated $^{32}$P-labeled ATP.

The oligonucleotide probes used to hybridize to the intron 2 region (IVS2+1) contained in the exon 2/intron 2 amplification products prepared above are shown below in Table 1. The sequences and corresponding SEQ ID NO for the oligonucleotide probes used in this screening and in Example 5 are listed below in Table 1. The probes that hybridized to the normal genes were designated Norm whereas the probes that hybridized to the mutated genes were designated Mut. The underlined nucleotide corresponds to the mutation nucleotide.

TABLE 1

| DESIGNATION | SEQ ID NO | SEQUENCE |
| --- | --- | --- |
| Intron 2 Norm | 10 | 5'-GGCATCAGGTGAGTGAG-3' |
| Intron 2 Mut | 5 | 5'-GGCATCAGATGAGTGAG-3' |
| Exon 2 Norm | 11 | 5'-ACAGGATTGCTTCTACT-3' |
| Exon 2 Mut | 12 | 5'-ACAGGATTGGCTTCTACT-3' |
| Exon 9 Norm | 13 | 5'-TACCCTAGAACCTCCTG-3' |
| Exon 9 Mut | 14 | 5'-TACCCTAGAGCCTCCTG-3' |
| Exon 10 Norm | 15 | 5'-GAACGACCTGGACGCAG-3' |
| Exon 10 Mut | 16 | 5'-GAACGACCCGGACGCAG-3' |

Ten X 10$^6$ cpm of the intron 2 normal and intron 2 mutant labeled probes were separately admixed with each filter. The nitrocellulose filters were then maintained overnight at 42° C. to allow for the formation of hybridization products. The nitrocellulose filters exposed to the intron 2 normal probe were washed with 6X SSC containing 0.1% SDS at 46° C. whereas the filters exposed to the intron 2 mutant probe were washed with the same solution at a more stringent temperature of 52° C. The nitrocellulose filters were then dried and subjected to radioautography.

The results of the allele specific oligonucleotide hybridization showed that amplified genomic DNA exon 2/intron 2 products having a guanine nucleotide in position 1 of intron 2 hybridized to the intron 2 normal probe. Only those intron 2 products having the point mutation of an adenine nucleotide at nucleotide position 1 hybridized with the mutant probe. Positive and negative controls were included in each assay to determine whether the PCR amplification was successful. Thus, the patients' genomic DNA prepared in Example 1 were determined by this alternative approach to have the unique point mutation of an adenine nucleotide substituted for a guanine nucleotide at the splice site at nucleotide position 1 in glucocerebrosidase intron 2.

5. Simultaneous Detection of an Insertion Mutation and Two Point Mutations in Genomic DNA from Gaucher Disease Patients A. Preparation of PCR Amplified Genomic DNA In addition to the insertion mutation in glucocerebrosidase exon 2, other single-base point mutations have been reported to cause Gaucher disease. See, Beutler et al., *Clin. Chim. Acta*, 194:161–166 (1990); Zirman et al., *Lancet*, ii:349–352 (1989); Tsuji et al., *N. Engl. J. Med.*, 316:570–621 (1987); Tsuji et al., *Proc. Natl. Acad. Sci., USA*, 85:2349–2352 (1988); Reiner et al., *DNA*, 7:107–116 (1988); Grabowski et al., *CRC Crit. Rev. Biochem Mol. Biol.*, 25:385–414 (1990); and Graves et al., *DNA* 7:521–528 (1988). The most common point mutation, also called a base substitution, occurs in exon 9 of the glucocerebrosidase gene at nucleotide position 2 which corresponds to cDNA nucleotide position 1226. At this position, an adenine nucleotide has been substituted by a guanine nucleotide. This mutation accounts for approximately 77% of the disease-causing alleles in Jewish patients exhibiting clinically significant Gaucher's disease. Another point mutation occurs in exon 10 of the glucocerebrosidase gene at nucleotide position 60 which corresponds to cDNA nucleotide position 1448. This mutation accounts for approximately 2% of the disease-causing alleles in Jewish Gaucher's disease patients. At this position, a thymine nucleotide has been substituted by a cytosine nucleotide.

An insertion mutation of an extra guanine nucleotide in exon 2 of glucocerebrosidase gene has recently been identified. Beutler et al., *Proc. Natl. Acad. Sci., USA*, 88:10544–10547 (1991). This mutation is present in approximately 13% of the Jewish population having Gaucher's disease. The inserted nucleotide occurs in exon 2 adjacent to nucleotide position 84 of the cDNA and adjacent to nucleotide position 57 of the genomic sequence. This mutation causes a frame-shift, the transcription of which results in the production of a termination codon and the consequent lack of the glucocerebrosidase protein.

The glucocerebrosidase pseudogene that is highly homologous with the functional glucocerebrosidase gene complicates detection of mutations that cause Gaucher disease. In order to detect mutations that were present on the functional gene, methods were developed to amplify regions of the functional gene without contamination from the pseudogene (Beutler et al., *Clin. Chim. Acta*, 194:161–166 (1990)). Recently, cDNAs that were cloned and sequenced from mRNA isolated from cultured skin fibroblasts of Gaucher disease patients revealed the presence of a fusion gene having a 5' end comprised of the functional gene and the 3' end comprised of the pseudogene (Zimran et al., *J. Clin. Invest.*, 85:219–222 (1990)). Thus, a cross-over between functional and non-functional pseudogenes had occurred.

As the point mutation (T→C) in exon 10 at nucleotide position 60 (cDNA 1448) is present in the pseudogene, it is advantageous, when screening for mutations in the population, to screen all genes including those fusion genes which contain certain mutations such as the one in exon 10. If a cross-over event occurs 5' or upstream of exon 10, the nucleotide position of the mutation in exon 10 will remain the same. However, if an unequal cross-over event occurs sufficiently 5' to the mutation, the nucleotide position of the mutation in exon 10 may change.

Based on the foregoing discussion, a preferred embodiment of this invention is the capacity to screen the glucocerebrosidase gene, the pseudogene and any fusion genes to obtain a improved analysis of the presence of mutations for correlation with the severity of the disease in a patient. The method for accomplishing the detection of the intron 2 (IVS2+1), exon 2, exon 9 and exon 10 mutations in both normal functional genes and fusion genes where a cross-over has occurred is presented below.

Genomic DNA was isolated from patients with Gaucher disease as described in Example 1. Two separate genomic DNA fragments of the glucocerebrosidase gene were then amplified with specific oligonucleotide primers shown in Table 2 below with the corresponding SEQ ID NOs.

TABLE 2

| DESIG-NATION | SEQ ID NO | SEQUENCE |
| --- | --- | --- |
| Exon 2 | 3 | 5'-GAATGTCCCAAGCCTTTGA-3' |
| Intron 2 | 4 | 5'-AAGCTGAAGCAAGAGAATCG-3' |
| Intron 7 | 8 | 5'-CAAGGTCCAGGATCAGTTGC-3' |
| Intron 10 | 9 | 5'-AACGCTGTCTTCAGCCCACT-3' |

The first genomic DNA fragment was amplified with the oligonucleotide primers designated exon 2 (a 5' anti-sense primer) and intron 2 (a 3' sense primer) as listed in Table 2. These primers when used in PCR amplification as described below resulted in the generation of a 358 base pair fragment in which both the intron 2 point mutation and the exon 2 insertion mutation (cDNA 84GG) could be identified, if present. Since the exon 2 oligonucleotide primer mismatched the pseudogene at two nucleotide positions and the intron 2 oligonucleotide primer was in a region which was deleted in the pseudogene, only the functional glucocerebrosidase gene was amplified with the exon 2 and intron 2 primer pair.

The second genomic DNA fragment was amplified with the oligonucleotide primers designated intron 7 (a 5' anti-sense primer) and intron 10 (a 3' sense primer) as listed in Table 2. These primers, when used in PCR amplification as described below, resulted in the generation of a 1353 base pair fragment in which both the exon 9 and 10 point mutations (cDNA 1226 and 1448, respectively) could be identified if present in the functional gene as well as in fusion cross-over genes. The intron 7 oligonucleotide primer mismatched the pseudogene at five nucleotide positions, therefore, only the functional gene was amplified. The intron 10 oligonucleotide primer, in contrast, matched both the functional gene and the pseudogene. Therefore, when the intron 10 primer was used in conjunction with the intron 7 primer, both functional genes and genes having cross-overs occurring between the regions of the two primers of the functional gene and the pseudogene, were amplified.

The PCR conditions used in the amplifying the resultant PCR products described above were performed as described in Example 3 with the exceptions that 180 ng of each oligonucleotide primer and 0.75 U of Taq DNA polymerase were used. Twenty-eight PCR cycles were performed as described in Example 3. The resultant PCR products were then blotted onto nitrocellulose filters as described in Example 4 for subsequent hybridization with labeled allele specific oligonucleotide probes as described below.

B. Detection of Mutations by Allele Specific Oligonucleotide Hybridization

The PCR products immobilized on nitrocellulose filters prepared in Example 5A above were treated under hybridization conditions as described in Example 4. The oligonucleotide probes used to detect the mutations in intron 2, exon 2, exon 9 and exon 10 are shown in Table 1 in Example 4. Both the normal and mutant probes were used to identify alleles having normal and mutant genotypes. The normal probes hybridized only to alleles that were normal in the region of the probe and whereas the mutant probes hybridized to only those alleles having the specific mutation. The results of the PCR amplification performed as described above on genomic DNA from Gaucher disease patients revealed that all four mutations could be amplified simultaneously from one PCR reaction and subsequently detected with allele specific oligonucleotide probes. Mutations present in the functional glucocerebrosidase gene as well as in fusion genes in which cross-overs between the functional glucocerebrosidase gene and pseudogene occurred between the two oligonucleotide primer pairs (intron 7 and intron 10) were readily detected using this protocol. Thus, the correlation of the presence of the mutations with the severity of the disease is more readily achieved with this preferred one step PCR amplification.

6. Advantages of a DNA-Based Analysis for Determining the Frequency of Gaucher Disease-Producing Alleles When a disease-producing gene exists at polymorphic levels in a population, the gene may be presumed to confer some selective advantage, especially among heterozygotes. When such a selective advantage exists, more than one mutation often achieves a high population frequency as seen in Gaucher disease where the exon 2 insertion mutation and exon 9 point mutation are expressed with a high frequency in the Jewish population. Although the vast majority of mutations may be regarded as being "public" in that they are found repeatedly in unrelated individuals, a baseline frequency of new "private" mutations will occur. Thus, disease diagnosis and or screening of heterozygotes can never be 100% accurate if based on the detection of specific, prevalent mutations. To know which disease alleles exist in the population and to assess their frequency requires the examination of large number of alleles. The invention described herein constitutes a rational approach to screening such a group and identifying new "private" mutations and in addition to identifying the relative frequency of both public and private mutations.

By screening DNA samples from 100 patients with Gaucher disease, of which 197 alleles were of Jewish origin, the discovery of the new mutation in intron 2 was achieved. As with several other mutations that cause Gaucher disease, the intron 2 mutation of an adenine nucleotide in the position normally occupied by a guanine nucleotide represents the normal pseudogene sequence. Therefore, both the normal glucocerebrosidase gene and the pseudogene lack exon 2 which results as a consequence of the mutation occurring in the 5 splice consensus site at nucleotide 1 of intron 2.

The IVS2+1 mutation was determined to be present in approximately 2.54% of the Jewish patients in clinical stages of Gaucher's disease. By screening for the four mutations present in intron 2, exon 2, exon 9 and exon 10, over 95% of the disease producing alleles have been identified at the DNA level in 97 Jewish and three half-Jewish subjects with Gaucher disease. Since the mutation in exon 9 (cDNA 1226G) is underrepresented in the patient population because not all homozygotes come to medical attention, screening the Ashkenazi population using DNA analysis for four mutations results in the detection of approximately 98% of all heterozygotes. The mutations in the glucocerebrosidase gene exist in two clusters where the exon 2 and intron 2 mutations occur at the 5' end and the exon 9 and exon 10 mutations occur at the 3' end. The clustering of the mutations facilitates the screening for all mutations based on PCR amplification of merely two segments of the gene in one convenient step using four separate oligonucleotide primers as described in Example 5. Thus, the invention described herein provides a means for the simultaneous detection of the novel point mutation in intron 2 in addition to the point mutations in exon 2, exon 9 and 10 in the glucocerebrosidase gene complex.

The foregoing specification, including the specific embodiments and examples, is intended to be illustrative of the present invention and is not to be taken as limiting. Numerous other variations and modifications can be effected without departing from the true spirit and scope of the invention.

---

What is claimed is:

1. A human genetic screening method for identifying a glucocerebrosidase gene mutation comprising detecting in a nucleic acid sample the presence of a glucocerebrosidase gene point mutation characterized as a substitution of an adenine nucleotide for a guanine nucleotide at nucleotide position 1 of glucocerebrosidase gene intron 2, thereby identifying said mutation.

2. The method according to claim 1 further comprising additionally detecting in a nucleic acid sample the presence of a glucocerebrosidase gene insertion mutation characterized as a insertion of an guanine nucleotide adjacent to nucleotide position 57 of glucocerebrosidase gene exon 2.

3. The method according to claim 1 further comprising additionally detecting in a nucleic acid sample the presence of a glucocerebrosidase gene point mutation characterized as a change from an adenine nucleotide to a guanine nucleotide at nucleotide position 2 of glucocerebrosidase gene exon 9.

4. The method according to claim 1 further comprising additionally detecting in a nucleic acid sample the presence of a glucocerebrosidase gene point mutation characterized as a change from a thymine nucleotide to a cytosine nucleotide at nucleotide position 60 of glucocerebrosidase gene exon 10.

5. A human genetic screening method for identifying a glucocerebrosidase gene mutation comprising:
   (a) treating, under amplification conditions, a sample of genomic DNA from a human with a polymerase chain reaction (PCR) primer pair for amplifying a region of human genomic DNA containing nucleotide position 1 of glucocerebrosidase gene intron 2, said treating producing an amplification product containing said region; and
   (b) detecting in the amplification product of step (a) the presence of an adenine (A) nucleotide point mutation at nucleotide position 1 of said intron, thereby identifying said mutation.

6. The method according to claim 5 wherein said region contains a nucleotide sequence represented by SEQ ID NO 2, or a fragment thereof.

7. The method according to claim 5 wherein said region consists essentially of a nucleotide sequence represented by SEQ ID NO 2.

8. The method according to claim 5 wherein said detecting comprises treating, under hybridization conditions, the amplification product of step (a) with an oligonucleotide probe specific for said point mutation, and detecting the formation of a hybridization product.

9. The method according to claim 8 wherein said oligonucleotide probe contains a nucleotide sequence represented by the formula, 5'-GGCATCAGATGAGTGAG-3' (SEQ ID NO 5).

10. The method according to claim 5 wherein said PCR primer pair produces an amplification product containing a preselected restriction enzyme site if said mutation is absent, and said detecting of step (b) comprises treating, under restriction conditions, the amplification product of step (a) with a restriction enzyme that recognizes said site, and detecting the presence of restriction products.

11. The method according to claim 5 wherein said PCR primer pair comprises:
   (i) a first primer that hybridizes to an anti-sense strand within a region of human genomic DNA corresponding to exon 2 at a location 5' to nucleotide 88 said exon; and
   (ii) a second primer that hybridizes to a sense strand of said intron 2 at a location 3' to nucleotide 1 of said intron.

12. The method according to claim 11 wherein said first primer of step (i) is represented by the formula, 5'-GAATGTCCCAAGCCTTTGA-3' (SEQ ID NO 3).

13. The method according to claim 11 wherein said second primer of step (ii) is represented by the formula, 5'-AAGCTGAAGCAAGAGAATCG-3' (SEQ ID NO 4).

14. The method according to claim 10 wherein said restriction enzyme is Hph I and said preselected restriction enzyme site is represented by the formula:
   5'-GGTGA(N)$_8$-3' (SEQ ID NO 6);
   3'-CCACT(N)$_7$-5' (SEQ ID NO 7);
where N can be A, C, G or T.

15. A method for detecting in a human a Gaucher disease allele containing a point mutation comprising substitution of an adenine (A) nucleotide for a guanine (G) at nucleotide position 1 of glucocerebrosidase gene intron 2, which method comprises:
   (a) forming a polymerase chain reaction (PCR) admixture by combining, in a PCR buffer, a sample of genomic DNA from said human and a glucocerebrosidase gene-specific PCR primer pair defined by 5' and 3+ primers, said 5' primer priming within a region of human genomic DNA corresponding to nucleotide positions 1-88 of glucocerebrosidase gene exon 2, and said 3' primer priming within a region of human genomic DNA corresponding to nucleotide positions 2-270 of said glucocerebrosidase gene intron 2;
   (b) subjecting said PCR admixture to a plurality of PCR thermocycles to produce a glucocerebrosidase gene amplification product;
   (c) treating, under hybridization products produced in step (c), thereby detecting said mutation.

16. The method according to claim 15 wherein said 5' primer of step (a) is represented by the formula, 5'-GAATGTCCCAAGCCTTTGA-3' (SEQ ID NO 3).

17. The method according to claim 15 wherein said 3' primer of step (a) is represented by the formula, 5'-AAGCTGAAGCAAGAGAATCG-3' (SEQ ID NO 4).

18. The method according to claim 15 wherein said probe of step (c) is represented by the formula, 5'-GGCATCAGATGAGTGAG-3' (SEQ ID NO 5).

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
    ( A ) LENGTH: 7620 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: exon
    ( B ) LOCATION: 356..611
    ( D ) OTHER INFORMATION: /product="Exon 1"

( i x ) FEATURE:
    ( A ) NAME/KEY: intron
    ( B ) LOCATION: 612..979
    ( D ) OTHER INFORMATION: /function="Intron 1"

( i x ) FEATURE:
    ( A ) NAME/KEY: exon
    ( B ) LOCATION: 980..1067
    ( D ) OTHER INFORMATION: /product="Exon 2"

( i x ) FEATURE:
    ( A ) NAME/KEY: intron
    ( B ) LOCATION: 1068..1619
    ( D ) OTHER INFORMATION: /function="Intron 2"

( i x ) FEATURE:
    ( A ) NAME/KEY: exon
    ( B ) LOCATION: 1620..1811
    ( D ) OTHER INFORMATION: /product="Exon 3"

( i x ) FEATURE:
    ( A ) NAME/KEY: intron
    ( B ) LOCATION: 1812..1934
    ( D ) OTHER INFORMATION: /function="Intron 3"

( i x ) FEATURE:
    ( A ) NAME/KEY: exon
    ( B ) LOCATION: 1935..2081
    ( D ) OTHER INFORMATION: /product="Exon 4"

( i x ) FEATURE:
    ( A ) NAME/KEY: intron
    ( B ) LOCATION: 2082..3046
    ( D ) OTHER INFORMATION: /function="Intron 4"

( i x ) FEATURE:
    ( A ) NAME/KEY: exon
    ( B ) LOCATION: 3047..3180
    ( D ) OTHER INFORMATION: /product="Exon 5"

( i x ) FEATURE:
    ( A ) NAME/KEY: intron
    ( B ) LOCATION: 3181..3390
    ( D ) OTHER INFORMATION: /function="Intron 5"

( i x ) FEATURE:
    ( A ) NAME/KEY: exon
    ( B ) LOCATION: 3391..3563
    ( D ) OTHER INFORMATION: /product="Exon 6"

( i x ) FEATURE:
    ( A ) NAME/KEY: intron
    ( B ) LOCATION: 3564..4116
    ( D ) OTHER INFORMATION: /function="Intron 6"

( i x ) FEATURE:
    ( A ) NAME/KEY: exon
    ( B ) LOCATION: 4117..4354
    ( D ) OTHER INFORMATION: /product="Exon 7"

( i x ) FEATURE:
    ( A ) NAME/KEY: intron
    ( B ) LOCATION: 4355..5227
    ( D ) OTHER INFORMATION: /function="Intron 7"

( i x ) FEATURE:
    ( A ) NAME/KEY: exon
    ( B ) LOCATION: 5228..5452
    ( D ) OTHER INFORMATION: /product="Exon 8"

( i x ) FEATURE:
    ( A ) NAME/KEY: intron
    ( B ) LOCATION: 5453..5852
    ( D ) OTHER INFORMATION: /function="Intron 8"

(ix) FEATURE:
    (A) NAME/KEY: exon
    (B) LOCATION: 5853..6016
    (D) OTHER INFORMATION: /product="Exon 9"

(ix) FEATURE:
    (A) NAME/KEY: intron
    (B) LOCATION: 6017..6385
    (D) OTHER INFORMATION: /function="Intron 9"

(ix) FEATURE:
    (A) NAME/KEY: exon
    (B) LOCATION: 6386..6502
    (D) OTHER INFORMATION: /product="Exon 10"

(ix) FEATURE:
    (A) NAME/KEY: intron
    (B) LOCATION: 6503..6596
    (D) OTHER INFORMATION: /function="Intron 10"

(ix) FEATURE:
    (A) NAME/KEY: exon
    (B) LOCATION: 6597..7245

(xi) SEQUENCE DESCRIPTION: SEQ ID NO:1:

```
GAGCTCTCCA TGCACACCTG TTACCGTTTC TGTCTTTATC TGTAAATATC TGTGTGTCTG      60
ACTTCCATGC CTCACACACC TCTATAGGGC AAAGACTGTC TTAAACATCT TGGTAGTGTC     120
AGTATTTTGC ACAGTGAAGT TTTTTTTTTT AAATTATATC AGCTTTATTT GTACCTTTTT     180
GACATTTCTA TCAAAAAAGA AGTGTGCCTG CTGTGGTTCC CATCCTCTGG GATTTAGGAG     240
CCTCTACCCC ATTCTCCATG CAAATCTGTG TTCTAGGCTC TTCCTAAAGT TGTCACCCAT     300
ACATGCCCTC CAGAGTTTTA TAGGGCATAT AATCTGTAAC AGATGAGAGG AAGCCAATTG     360
CCCTTTAGAA ATATGGCTGT GATTGCCTCA CTTCCTGTGT CATGTGACGC TCCTAGTCAT     420
CACATGACCC ATCCACATCG GGAAGCCGGA ATTACTTGCA GGGCTAACCT AGTGCCTATA     480
GCTAAGGCAG GTACCTGCAT CCTTGTTTTT GTTTAGTGGA TCCTCTATCC TTCAGAGACT     540
CTGGAACCCC TGTGGTCTTC TCTTCATCTA ATGACCCTGA GGGGATGGAG TTTTCAAGTC     600
CTTCCAGAGA GGTAAGAGAG AGAGCTCCCA ATCAGCATTG TCACAGTGCT TCTGGAATCC     660
TGGCACTGGA ATTTAATGAA TGACAGACTC TCTTTGAATC CAGGGCCATC ATGGCTCTTT     720
GAGCAAGGCA CAGATGGAGG GAGGGGTCGA AGTTGAAATG GGTGGGAAGA GTGGTGGGGA     780
GCATCCTGAT TTGGGGTGGG CAGAGAGTTG TCATCAGAAG GGTTGCAGGG AGAGCTGCAC     840
CCAGGTTTCT GTGGGCCTTG TCCTAATGAA TGTGGGAGAC CGGGCCATGG GCACCCAAAG     900
GCAGCTAAGC CCTGCCCAGG AGAGTAGTTG AGGGGTGGAG AGGGGCTTGC TTTTCAGTCA     960
TTCCTCATTC TGTCCTCAGG AATGTCCCAA GCCTTTGAGT AGGGTAAGCA TCATGGCTGG    1020
CAGCCTCACA GGATTGCTTC TACTTCAGGC AGTGTCGTGG CATCAGGTG  AGTGAGTCAA    1080
GGCAGTGGGG AGGTAGCACA GAGCCTCCCT TCTGCCTCAT AGTCCTTTGG TAGCCTTCCA    1140
GTAAGCTGGT GGTAGACTTT TAGTAGGTGC TCAATAAATC CTTTTGAGTG ACTGAGACCA    1200
ACTTTGGGGT GAGGATTTTG TTTTTTTTCT TTTGAAACAG AGTCTTACTC TGTTGCCTGG    1260
GCTGGAGTGC AGTGGTGCAA TTTTGGCTCA TTCCAACCTC TGCCTCCCAG ATTCAAGCGA    1320
TTCTCTTGCT TCAGCTTCCC AGGTAGCTGG GATTACAGGC GGCCACCACT ACGCCCAGCT    1380
AATTTTTGTA TTTTTAGTAG AGACGGGGTT TCACCATGCT GGCAAGGCAG GTCTCAAACT    1440
CCTCACCTCA GGTGATCCGC CCACCTCGGC CTCCTAAAGT GCTAGGATTA CAGGTGTGAG    1500
CCCCTGCGCC CGGCCAAGGG GTGAGGAATT TGAAACCGT  GTTCAGTCTC TCCTAGCAGA    1560
TGTGTCCATT CTCCATGTCT TCATCAGACC TCACTCTGCT TGTACTCCCT CCCTCCCAGG    1620
TGCCCGCCCC TGCATCCCTA AAAGCTTCGG CTACAGCTCG GTGGTGTGTG TCTGCAATGC    1680
```

| | | | | | |
|---|---|---|---|---|---|
| CACATACTGT | GACTCCTTTG | ACCCCCCGAC | CTTTCCTGCC | CTTGGTACCT | TCAGCCGCTA | 1740 |
| TGAGAGTACA | CGCAGTGGGC | GACGGATGGA | GCTGAGTATG | GGGCCCATCC | AGGCTAATCA | 1800 |
| CACGGGCACA | GGTAACCATT | ACACCCCTCA | CCCCCTGGGC | CAGGCTGGGT | CCTCCTAGAG | 1860 |
| GTAAATGGTG | TCAGTGATCA | CCATGGAGTT | TCCCGCTGGG | TACTGATACC | CTTATTCCCT | 1920 |
| GTGGATGTCC | TCAGGCCTGC | TACTGACCCT | GCAGCCAGAA | CAGAAGTTCC | AGAAAGTGAA | 1980 |
| GGGATTTGGA | GGGGCCATGA | CAGATGCTGC | TGCTCTCAAC | ATCCTTGCCC | TGTCACCCCC | 2040 |
| TGCCCAAAAT | TTGCTACTTA | AATCGTACTT | CTCTGAAGAA | GGTGAGGAGG | AAGGGGACAA | 2100 |
| GATGACATAG | AGCCATTGAA | ACTTTTCATT | TTTCTTTTCT | TTTTTAAAA | TTTTTTGAG | 2160 |
| GCAGAATCTC | ACTCTGCCCA | TTCTGTCGGC | GAGACAGGAG | TGCAGTGGTG | TGATCTCCCC | 2220 |
| TCACAGCAAC | CTCTGCCTCC | CAGGCTATAG | TGATTCTCCT | GCCTCAGCCT | CCTGAGTAGC | 2280 |
| TGGAATTATA | GGCGTGCGCC | ACTACCACCT | GGCTAATTTT | TGTATTTTA | GTAGAGACAG | 2340 |
| GGTTTCATCA | TGTTGACCAG | GCTAGTCTTA | AACTCCTGAC | CTCAAATGAT | ATACCTGCCT | 2400 |
| TGGCCTCCCG | AAGTGCTGGA | ATTACAAGTG | TGAGCCACCG | AGCCCAGCAG | ACACTTTTCT | 2460 |
| TTTTTCTTTT | TTTTTTTTG | AGACAGAGTC | TCGCACTGTC | ACCCAGGCTG | GAGTGCAGTG | 2520 |
| GCACAATCTC | AGCTCACTGC | AACCTCCACC | TCCCGGGTTC | AGGTGATTCT | CCTGTCTCAG | 2580 |
| CCTCTCGAGT | ACCTGGGATT | ACAGGTGCCT | GCCACCACGC | CCGGCTAATT | TTTTGTATTT | 2640 |
| TTAGTAGAGA | CAGGGTTTCA | CTATGTTGGC | CAGGATGATT | GCGAACTCCT | GACCTCGTGA | 2700 |
| TCTGCCCACA | TCGGCCTCCC | AAAGTGCTGG | GATTACATGC | GTGAGCCACT | GACACTTTTC | 2760 |
| TTTGCCCTTT | CTTTGGACCC | TGACTTCTGC | CCATCCCTGA | CATTTGGTTC | CTGTTTTAAT | 2820 |
| GCCCTGTGAA | ATAAGATTTC | CCCGCCTATC | ATCTGCTAAC | TGCTACGGAC | TCAGGCTCAG | 2880 |
| AAAGGCCTGC | GCTTCACCCA | GGTGCCAGCC | TCCACAGGTT | CCAACCCAGG | AGCCCAAGTT | 2940 |
| CCCTTTGGCC | CTGACTCAGA | CACTATTAGG | ACTGGCAAGT | GATAAGCAGA | GTCCCATACT | 3000 |
| CTCCTATTGA | CTCGGACTAC | CATATCTTGA | TCATCCTTTT | CTGTAGGAAT | CGGATATAAC | 3060 |
| ATCATCCGGG | TACCCATGGC | CAGCTGTGAC | TTCTCCATCC | GCACCTACAC | CTATGCAGAC | 3120 |
| ACCCCTGATG | ATTTCCAGTT | GCACAACTTC | AGCCTCCCAG | AGGAAGATAC | CAAGCTCAAG | 3180 |
| GTAGGCATTC | TAGCTTTTTC | AGGCCCTGAG | GGCCCTGATG | TCTGGGGGTT | GAGAAACTGT | 3240 |
| AGGGTAGGTC | TGCTTGTACA | GACATTTGT | CCCCTGCTGT | TTTGTCCTGG | GGGTGGGAGG | 3300 |
| GTGGGGGCTA | ATGGCTGAAC | CGGATGCACT | GGTTGGGCTA | GTATGTGTTC | CAACTCTGGG | 3360 |
| TGCTTCTCTC | TTCACTACCT | TTGTCTCTAG | ATACCCCTGA | TTCACCGAGC | CCTGCAGTTG | 3420 |
| GCCCAGCGTC | CCGTTTCACT | CCTTGCCAGC | CCCTGGACAT | CACCCACTTG | GCTCAAGACC | 3480 |
| AATGGAGCGG | TGAATGGGAA | GGGGTCACTC | AAGGGACAGC | CCGGAGACAT | CTACCACCAG | 3540 |
| ACCTGGGCCA | GATACTTTGT | GAAGTAAGGG | ATCAGCAAGG | ATGTGGGATC | AGGACTGGCC | 3600 |
| TCCCATTTAG | CCATGCTGAT | CTGTGTCCCA | ACCCTCAACC | TAGTTCCACT | TCCAGATCTG | 3660 |
| CCTGTCCTCA | GCTCACCTTT | CTACCTTCTG | GGCCTTTCAG | CCTTGGGCCT | GTCAATCTTG | 3720 |
| CCCACTCCAT | CAGGCTTCCT | GTTCTCTCGG | TCTGGCCCAC | TTTCTTTTTA | TTTTTCTTCT | 3780 |
| TTTTTTTTTT | TTTGAGAAGG | AGTCTCTCTC | TCTGTCACCC | AGGCTGGAGT | GCTGTGGCGC | 3840 |
| CATCTTCACT | CACTGTAACC | TTTGCCTCCT | GAGTTCAAGC | AATTCTCCTG | CCTCAGCCTT | 3900 |
| CCAAGTAGCT | GGGATATAGG | CGCCTGCCAC | CAGGCCCGGC | TGATTTTTCT | ATTTTTAGTA | 3960 |
| GAGACGGGGT | TTCGCCAGGC | TGTTCTCGAC | TCCTGAACTC | AAGTGATCCA | CCTGCCTCGG | 4020 |
| CTTCCCAAAG | TGCTGGGATT | ACAGGTGTGA | GCCACCACAC | CCAGCTGGTC | TGGTCCACTT | 4080 |
| TCTTGGCCGG | ATCATTCATG | ACCTTTCTCT | TGCCAGGTTC | CTGGATGCCT | ATGCTGAGCA | 4140 |

```
CAAGTTACAG  TTCTGGGCAG  TGACAGCTGA  AAATGAGCCT  TCTGCTGGGC  TGTTGAGTGG    4200
ATACCCCTTC  CAGTGCCTGG  GCTTCACCCC  TGAACATCAG  CGAGACTTCA  TTGCCCGTGA    4260
CCTAGGTCCT  ACCCTCGCCA  ACAGTACTCA  CCACAATGTC  CGCCTACTCA  TGCTGGATGA    4320
CCAACGCTTG  CTGCTGCCCC  ACTGGGCAAA  GGTGGTAAGG  CCTGGACCTC  CATGGTGCTC    4380
CAGTGACCTT  CAAATCCAGC  ATCCAAATGA  CTGGCTCCCA  AACTTAGAGC  GATTTCTCTA    4440
CCCAACTATG  GATTCCTAGA  GCACCATTCC  CCTGGACCTC  CAGGGTGCCA  TGGATCCCAC    4500
AGTTGTCGCT  TGAAACCTTT  CTAGGGGCTG  GGCGAGGTGG  CTCACTCATG  CAAACCCAGC    4560
ACTTTGGGAA  GCCGAGGCGG  GTGATCACCT  GAGGTCAGGA  GTTTAAGACC  ACCCTGGCCA    4620
ACGTGTTGAA  ACCCTGTGTC  TACTAAAATA  CAAAAAAAAA  AAATTATCTG  GGCATGATGG    4680
TGGGTGTCTG  TAATCCCAGC  TACTCAGGAG  GCTGAGAAGG  GAGAATCAGT  TGAACCCGGG    4740
AGATGGTGGT  TGCGGTGAGC  CGAGATCGCG  CCACTGCACT  CCAGCCTGGG  AGGCTGAGCG    4800
AGACTCCATC  TCGAAACCAA  AACAAAACAA  AACTATCTAG  GCTGGGGGTG  GTGGTTCATG    4860
TATGTATGTG  TATATACATA  TATATGTGTT  TATATGGTAT  ATATATATAC  ACACACACAC    4920
ATACATACAC  ACACATACAC  ACACAAATTA  GCTGGGTGTG  GCACCCGTGT  AGTCCCAGCT    4980
ACTCAGGAGG  CTAATGTGGG  AGGATCAGTT  GACCCTAGGA  AGTCAAGGCT  GCAGTGAGTC    5040
GTGATTGCGC  CACTGTACTC  CAGCCCGAGT  GACAGAGTGA  CATCCTGTCT  CAAAAACAAA    5100
AAAAAATCTC  CCCAAACCTC  TCTAGTTGCA  TTCTTCCCGT  CACCCACCTC  CAGGATTCCT    5160
ACAACAGGAA  CTAGAAGTTC  CAGAAGCCTG  TGTGCAAGGT  CCAGGATCAG  TTGCTCTTCC    5220
TTTGCAGGTA  CTGACAGACC  CAGAAGCAGC  TAAATATGTT  CATGGCATTG  CTGTACATTG    5280
GTACCTGGAC  TTTCTGGCTC  CAGCCAAAGC  CACCCTAGGG  GAGACACACC  GCCTGTTCCC    5340
CAACACCATG  CTCTTTGCCT  CAGAGGCCTG  TGTGGGCTCC  AAGTTCTGGG  AGCAGAGTGT    5400
GCGGCTAGGC  TCCTGGGATC  GAGGGATGCA  GTACAGCCAC  AGCATCATCA  CGGTAAGCCA    5460
CCCCAGTCTC  CCTTCCTGCA  AAGCAGACCT  CAGACCTCTT  ACTAGTTTCA  CCAAAGACTG    5520
ACAGAAGCCC  TTCCTGTCCA  GCTTTCCCCA  GCTAGCCTGC  CCTTTTGAGC  AACTCTGGGG    5580
AACCATGATT  CCCTATCTTC  CCTTTCCTTC  ACAGGTCTGC  ACACCTCATT  GCCCCTTTTG    5640
CAACTACTGA  GGCACTTGCA  GCTGCCTCAG  ACTTCTCAGC  TCCCCTTGAG  ATGCCTGGAT    5700
CTTCACACCC  CCAACTCCTT  AGCTACTAAG  GAATGTGCCC  CTCACAGGGC  TGACCTACCC    5760
ACAGCTGCCT  CTCCCACATG  TGACCCTTAC  CTACACTCTC  TGGGGACCCC  CAGTGTTGAG    5820
CCTTTGTCTC  TTTGCCTTTG  TCCTTACCCT  AGAACCTCCT  GTACCATGTG  GTCGGCTGGA    5880
CCGACTGGAA  CCTTGCCCTG  AACCCCGAAG  GAGGACCCAA  TTGGGTGCGT  AACTTTGTCG    5940
ACAGTCCCAT  CATTGTAGAC  ATCACCAAGG  ACACGTTTTA  CAAACAGCCC  ATGTTCTACC    6000
ACCTTGGCCA  CTTCAGGTGA  GTGGAGGGCG  GGCACCCCCA  TTCCATACCA  GGCCTATCAT    6060
CTCCTACATC  GGATGGCTTA  CATCACTCTA  CACCACGAGG  GAGCAGGAAG  GTGTTCAGGG    6120
TGGAACCTCG  GAAGAGGCAC  ACCCATCCCC  TTTTGCGCCA  TGGAGGCAGG  AAGTGACTAG    6180
GTAGCAACAG  AAAACCCCAA  TGCCTGAGGC  TGGACTGCGA  TGCAGAAAAG  CAGGGTCAGT    6240
GCCCAGCAGC  ATGGCTCCAG  GCCTAGAGAG  CCAGGGCAGA  GCCTCTGCAG  GAGTTATGGG    6300
GTGGGTCCGT  GGGTGGGTGA  CTTCTTAGAT  GAGGGTTTCA  TGGGAGGTAC  CCCGAGGGAC    6360
TCTGACCATC  TGTTCCCACA  TTCAGCAAGT  TCATTCCTGA  GGGCTCCCAG  AGAGTGGGGC    6420
TGGTTGCCAG  TCAGAAGAAC  GACCTGGACG  CAGTGGCACT  GATGCATCCC  GATGGCTCTG    6480
CTGTTGTGGT  CGTGCTAAAC  CGGTGAGGGC  AATGGTGAGG  TCTGGGAAGT  GGGCTGAAGA    6540
CAGCGTTGGG  GGCCTTGGCA  GGATCACACT  CTCAGCTTCT  CCTCCCTGCT  CCCTAGCTCC    6600
```

-continued

| | | | | | |
|---|---|---|---|---|---|
| TCTAAGGATG | TGCCTCTTAC | CATCAAGGAT | CCTGCTGTGG | GCTTCCTGGA | GACAATCTCA | 6660
| CCTGGCTACT | CCATTCACAC | CTACCTGTGG | CGTCGCCAGT | GATGGAGCAG | ATACTCAAGG | 6720
| AGGCACTGGG | CTCAGCCTGG | GCATTAAAGG | GACAGAGTCA | GCTCACACGC | TGTCTGTGAC | 6780
| TAAAGAGGGC | ACAGCAGGGC | CAGTGTGAGC | TTACAGCGAC | GTAAGCCAG | GGGCAATGGT | 6840
| TTGGGTGACT | CACTTTCCCC | TCTAGGTGGT | GCCAGGGGCT | GGAGGCCCCT | AGAAAAGAT | 6900
| CAGTAAGCCC | CAGTGTCCCC | CCAGCCCCCA | TGCTTATGTG | AACATGCGCT | GTGTGCTGCT | 6960
| TGCTTTGGAA | ACTGGGCCTG | GGTCCAGGCC | TAGGGTGAGC | TCACTGTCCG | TACAAACACA | 7020
| AGATCAGGGC | TGAGGGTAAG | GAAAAGAAGA | GACTAGGAAA | GCTGGGCCCA | AAACTGGAGA | 7080
| CTGTTTGTCT | TTCCTGGAGA | TGCAGAACTG | GGCCCGTGGA | GCAGCAGTGT | CAGCATCAGG | 7140
| GCGGAAGCCT | TAAAGCAGCA | GCGGGTGTGC | CCAGGCACCC | AGATGATTCC | TATGGCACCA | 7200
| GCCAGGAAAA | ATGGCAGCTC | TTAAAGGAGA | AAATGTTTGA | GCCCAGTCAG | TGTGAGTGGC | 7260
| TTTATTCTGG | GTGGCAGCAC | CCCGTGTCCG | GCTGTACCAA | CAACGAGGAG | GCACGGGGGC | 7320
| CTCTGGAATG | CATGAGAGTA | GAAAACCAG | TCTTGGGAGC | GTGAGGACAA | ATCATTCCTC | 7380
| TTCATCCTCC | TCAGCCATGC | CCAGGGTCCG | GGTGCCTGGG | GCCCGAGCAG | GCGTTGCCCG | 7440
| CTGGATGGAG | ACAATGCCGC | TGAGCAAGGC | GTAGCCACCA | TGGCTGCCAG | TCCTGCCAGC | 7500
| ACAGATAGGA | TCTGGTTCCG | GCGCCGGTAT | GGCTCCTCCT | CAGTCTCTGG | GCCTGCTGGT | 7560
| GTCTGGCGTT | GCGGTGGTAC | CTCAGCTGAG | GGTCAAGGAA | GGAAGGTGTG | TTAGGAGAAC | 7620

( 2 ) INFORMATION FOR SEQ ID NO:2:

( i ) SEQUENCE CHARACTERISTICS:
        ( A ) LENGTH: 358 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

| | | | | | |
|---|---|---|---|---|---|
| GAATGTCCCA | AGCCTTTGAG | TAGGGTAAGC | ATCATGGCTG | GCAGCCTCAC | AGGATTGCTT | 60
| CTACTTCAGG | CAGTGTCGTG | GGCATCAGAT | GAGTGAGTCA | AGGCAGTGGG | GAGGTAGCAC | 120
| AGAGCCTCCC | TTCTGCCTCA | TAGTCCTTTG | GTAGCCTTCC | AGTAAGCTGG | TGGTAGACTT | 180
| TTAGTAGGTG | CTCAATAAAT | CCTTTTGAGT | GACTGAGACC | AACTTTGGGG | TGAGGATTTT | 240
| GTTTTTTTTC | TTTTGAAACA | GAGTCTTACT | CTGTTGCCTG | GGCTGGAGTG | CAGTGGTGCA | 300
| ATTTTGGCTC | ATTCCAACCT | CTGCCTCCCA | GATTCAAGCG | ATTCTCTTGC | TTCAGCTT | 358

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GAATGTCCCA AGCCTTTGA                                                                            19

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AAGCTGAAGC AAGAGAATCG     20

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GGCATCAGAT GAGTGAG     17

( 2 ) INFORMATION FOR SEQ ID NO:6:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGTGANNNNN NNN     13

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CCTCTNNNNN NN     12

( 2 ) INFORMATION FOR SEQ ID NO:8:

( i ) SEQUENCE CHARACTERISTICS:
        ( A ) LENGTH: 20 base pairs (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

CAAGGTCCAG GATCAGTTGC                                                                                   20

(2) INFORMATION FOR SEQ ID NO:9:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

AACGCTGTCT TCAGCCCACT                                                                                   20

(2) INFORMATION FOR SEQ ID NO:10:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GGCATCAGGT GAGTGAG                                                                                      17

(2) INFORMATION FOR SEQ ID NO:11:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

ACAGGATTGC TTCTACT                                                                                      17

(2) INFORMATION FOR SEQ ID NO:12:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(i i i) HYPOTHETICAL: NO (i v) ANTI-SENSE: NO (x i) SEQUENCE DESCRIPTION: SEQ ID NO:12:

ACAGGATTGG CTTCTACT 18

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:13:

TACCCTAGAA CCTCCTG 17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:14:

TACCCTAGAG CCTCCTG 17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:15:

GAACGACCTG GACGCAG 17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:16:

GAACGACCCG GACGCAG 17

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

TCAAGACCAA TGGAGCGGTG 20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

CTAGGTCACG GGCAATGAAG 20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

ACTGTCGACA AAGTTACGCA 20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

CTCTGGAACC CCTGTGGTCT 20

( 2 ) INFORMATION FOR SEQ ID NO:21:

( i ) SEQUENCE CHARACTERISTICS:

(A) LENGTH: 20 base pairs
  (B) TYPE: nucleic acid
  (C) STRANDEDNESS: single
  (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

GGGTCCTCCT TCGGGGTTCA 20

( 2 ) INFORMATION FOR SEQ ID NO:22:

( i ) SEQUENCE CHARACTERISTICS:
    (A) LENGTH: 20 base pairs
    (B) TYPE: nucleic acid
    (C) STRANDEDNESS: single
    (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

CTCTTCATCT AATGACCCTG 20

( 2 ) INFORMATION FOR SEQ ID NO:23:

( i ) SEQUENCE CHARACTERISTICS:
    (A) LENGTH: 20 base pairs
    (B) TYPE: nucleic acid
    (C) STRANDEDNESS: single
    (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

CTAGGTCACG GGCAATGAAG 20

( 2 ) INFORMATION FOR SEQ ID NO:24:

( i ) SEQUENCE CHARACTERISTICS:
    (A) LENGTH: 20 base pairs
    (B) TYPE: nucleic acid
    (C) STRANDEDNESS: single
    (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

GCTCCACGGG CCCAGTTCTG 20

( 2 ) INFORMATION FOR SEQ ID NO:25:

( i ) SEQUENCE CHARACTERISTICS:
    (A) LENGTH: 20 base pairs
    (B) TYPE: nucleic acid
    (C) STRANDEDNESS: single
    (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

CATCATCCGG GTACCCATGG　　　　　　　　　　　　　　　　　　　　　　20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

ATGGGGCTG GGGGGACACT　　　　　　　　　　　　　　　　　　　　　　　20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

ACCCCTGAAC ATCAGCGAGA　　　　　　　　　　　　　　　　　　　　　　20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

GCCCAGTGCC TCCTTGAGTA　　　　　　　　　　　　　　　　　　　　　　20